(12) United States Patent
Deshpande et al.

(10) Patent No.: US 9,822,115 B2
(45) Date of Patent: Nov. 21, 2017

(54) NITROGEN CONTAINING COMPOUNDS AND THEIR USE AS ANTIBACTERIAL AGENTS

(71) Applicant: WOCKHARDT LIMITED, Aurangabad (IN)

(72) Inventors: Prasad Keshav Deshpande, Aurangabad (IN); Satish Bhawsar, Aurangabad (IN); Sanjay Raikar, Aurangabad (IN); Sanjay Kisan Dabhade, Pune (IN); Laxmikant Pavase, Ahmednagar (IN); Amit Mishra, Lucknow (IN); Sunil Gupta, Kota (IN); Vikas Vitthalrao Deshmukh, Ahmednagar (IN); Sunil Bhaginath Jadhav, Ahmednagar (IN); Rajesh Kale, Amravati (IN); Sachin Bhagwat, Aurangabad (IN); Ravindra Dattatraya Yeole, Aurangabad (IN); Mahesh Vithalbhai Patel, Aurangabad (IN)

(73) Assignee: WOCKHARDT LIMITED, Aurangabad (IN)

( * ) Notice: Subject to any disclaimer, the term of this patent is extended or adjusted under 35 U.S.C. 154(b) by 0 days.

(21) Appl. No.: 15/107,409

(22) PCT Filed: Jan. 21, 2015

(86) PCT No.: PCT/IB2015/050466
§ 371 (c)(1),
(2) Date: Jun. 22, 2016

(87) PCT Pub. No.: WO2015/110969
PCT Pub. Date: Jul. 30, 2015

(65) Prior Publication Data
US 2016/0355516 A1    Dec. 8, 2016

(30) Foreign Application Priority Data

Jan. 21, 2014   (IN) .......................... 192/MUM/2014

(51) Int. Cl.
| | | |
|---|---|---|
| C07D 471/08 | (2006.01) |
| A61K 31/407 | (2006.01) |
| A61K 31/424 | (2006.01) |
| A61K 45/06 | (2006.01) |
| A61K 31/445 | (2006.01) |
| A61K 31/496 | (2006.01) |
| C07F 7/18 | (2006.01) |
| A61K 31/439 | (2006.01) |
| A61K 31/546 | (2006.01) |
| A61K 31/695 | (2006.01) |

(52) U.S. Cl.
CPC .......... *C07D 471/08* (2013.01); *A61K 31/407* (2013.01); *A61K 31/424* (2013.01); *A61K 31/439* (2013.01); *A61K 31/445* (2013.01); *A61K 31/496* (2013.01); *A61K 31/546* (2013.01); *A61K 31/695* (2013.01); *A61K 45/06* (2013.01); *C07F 7/1856* (2013.01)

(58) Field of Classification Search
None
See application file for complete search history.

(56) References Cited

U.S. PATENT DOCUMENTS

2013/0225554 A1    8/2013  Maiti et al.

FOREIGN PATENT DOCUMENTS

| WO | WO2013030733 A1 | 3/2013 |
| WO | WO2013180197 A1 | 12/2013 |

*Primary Examiner* — Brian J Davis
(74) *Attorney, Agent, or Firm* — Bio Intellectual Property Servives LLC;(Bio IPS); O. (Sam) Zaghmout

(57) ABSTRACT

Compounds of Formula (I), their preparation, and use in preventing or treating a bacterial infection are disclosed. (I)

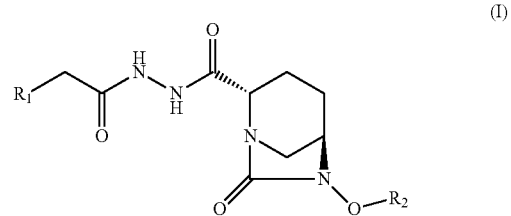

20 Claims, No Drawings

NITROGEN CONTAINING COMPOUNDS AND THEIR USE AS ANTIBACTERIAL AGENTS

RELATED PATENT APPLICATIONS

This application claims priority to Indian Patent Application No. 192/MUM/2014 filed on Jan. 21, 2014, the disclosures of which are incorporated herein by reference in its entirety as if fully rewritten herein.

FIELD OF THE INVENTION

The invention relates to nitrogen containing compounds, their preparation and their use in preventing or treating infections.

BACKGROUND OF INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistant. Coates et al. (*Br. J. Pharmacol.* 2007; 152(8), 1147-1154.) have reviewed novel approaches to developing new antibiotics. However, the development of new antibacterial agents is a challenging task. For example, Gwynn et al. (*Annals of the New York Academy of Sciences,* 2010, 1213: 5-19) have reviewed the challenges in discovery of antibacterial agents.

Several compounds have been described in the prior art for use in treatment of bacterial infections (for example, see Patent Application Nos. PCT/IB2012/054296, PCT/IB2012/054290, US20130225554, PCT/US2010/060923, PCT/EP2010/067647, PCT/US2010/052109, PCT/US2010/048109, PCT/GB2009/050609, PCT/EP2009/056178, PCT/US2009/041200, PCT/IB2013/053092 and PCT/IB2012054706). However, there remains a need for potent antibacterial agents for preventing and/or treating bacterial infections, including those caused by bacteria that are resistant to known antibacterial agents.

The inventors have now surprisingly discovered novel nitrogen containing compounds having potent antibacterial activity.

SUMMARY OF THE INVENTION

Accordingly, there are provided nitrogen containing compounds, methods for preparation of these compounds, pharmaceutical compositions comprising these compounds, and method for preventing or treating a bacterial infection in a subject using these compounds.

In one general aspect, there are provided compounds of Formula (I):

Formula (I)

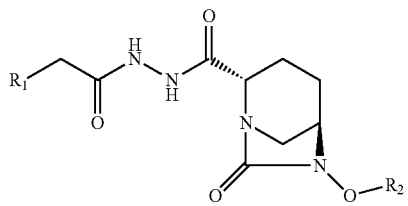

or a stereoisomer or a pharmaceutically acceptable derivative thereof;
wherein:
$R_1$ is:
(a) $C_1$-$C_6$ alkyl optionally substituted with one or more substituents independently selected from $C_1$-$C_6$ alkyl, halogen, CN, $OR_3$, $NR_3R_4$, $CONR_3R_4$, cycloalkyl, heterocycloalkyl, aryl, or heteroaryl;
(b) aryl optionally substituted with one or more substituents independently selected from $C_1$-$C_6$ alkyl, halogen, CN, $OR_3$, $NR_3R_4$, or $CONR_3R_4$, or
(c) heteroaryl optionally substituted with one or more substituents independently selected from $C_1$-$C_6$ alkyl, halogen, CN, $OR_3$, $NR_3R_4$, or $CONR_3R_4$;
$R_2$ is:
(a) $SO_3M$,
(b) $CF_2COOM$,
(c) CHFCOOM,
(d) $CH_2COOM$, or
(e) $CF_3$;
$R_3$ and $R_4$ are each independently:
(a) hydrogen, or
(b) $C_1$-$C_6$ alkyl optionally substituted with one or more substituents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ alkyl), CON($C_1$-$C_6$ alkyl)$_2$, cycloalkyl, heterocycloalkyl, aryl or heteroaryl;
M is hydrogen or a cation.

In another general aspect, there are provided pharmaceutical compositions comprising a compound of Formula (I) or a stereoisomer or a pharmaceutically acceptable derivative thereof.

In another general aspect, there is provided a method for preventing or treating a bacterial infection in a subject, said method comprising administering to said subject a compound of Formula (I) or a stereoisomer or a pharmaceutically acceptable derivative thereof.

In yet another general aspect, there is provided a method for preventing or treating a bacterial infection in a subject, said method comprising administering to said subject a pharmaceutical composition comprising a compound of Formula (I) or a stereoisomer or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one beta-lacatamse inhibitor or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In another general aspect, there are provided pharmaceutical compositions comprising: (a) a compound of Formula (I) or a stereoisomer or a pharmaceutically acceptable derivative thereof, (b) at least one beta-lacatamse inhibitor or a pharmaceutically acceptable derivative thereof, and (c) at least one antibacterial agent or a pharmaceutically acceptable derivative thereof.

In another general aspect, there is provided a method for preventing or treating a bacterial infection in a subject, said method comprising administering to said subject a pharmaceutical composition comprising: (a) a compound of Formula (I) or a stereoisomer or a pharmaceutically acceptable derivative thereof, and (b) at least one beta-lactamase inhibitor or a pharmaceutically acceptable derivative thereof.

In another general aspect, there is provided a method for preventing or treating a bacterial infection in a subject, said method comprising administering to said subject a pharmaceutical composition comprising: (a) a compound of Formula (I) or a stereoisomer or a pharmaceutically acceptable derivative thereof, and (b) at least one antibacterial agent or pharmaceutically acceptable derivative thereof.

In another aspect, there is provided a method for preventing or treating a bacterial infection in a subject, said method comprising administering to said subject a pharmaceutical composition comprising: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or a pharmaceutically acceptable derivative thereof.

In another general aspect, there is provided a method for preventing or treating a bacterial infection in a subject, said method comprising administering to said subject: (a) a compound of Formula (I) or a stereoisomer or a pharmaceutically acceptable derivative thereof, and (b) at least one beta-lactamase inhibitor, or pharmaceutically acceptable derivative thereof.

In another general aspect, there is provided a method for preventing or treating a bacterial infection in a subject, said method comprising administering to said subject: (a) a compound of Formula (I) or a stereoisomer or a pharmaceutically acceptable derivative thereof, and (b) at least one antibacterial agent or pharmaceutically acceptable derivative thereof.

In another general aspect, there is provided a method for preventing or treating a bacterial infection in a subject, said method comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In another general aspect, there are provided methods for increasing antibacterial effectiveness of an antibacterial agent in a subject, said method comprising co-administering said antibacterial agent, or a pharmaceutically acceptable derivative thereof, with a compound of Formula (I), or a stereoisomer or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "$C_1$-$C_6$ alkyl" as used herein refers to branched or unbranched acyclic hydrocarbon radical with 1 to 6 carbon atoms. Typical non-limiting examples of "$C_1$-$C_6$ alkyl" include methyl, ethyl, n-propyl, iso-propyl, n-butyl, sec-butyl, iso-butyl, tert-butyl, n-pentyl, iso-pentyl, tert-pentyl, neopentyl, sec-pentyl, 3-pentyl, n-hexyl, 2-methylpentyl, 3-methylpentyl, 2,2-dimethylbutyl, 2,3-dimethylbutyl and the like. The "$C_1$-$C_6$ alkyl" may be unsubstituted, or substituted with one or more substituents. Typical, non-limiting examples of such substituents include halogen, alkoxy, CN, SH, COOH, COOC$_1$-C$_6$alkyl, CONH$_2$, OH, NH$_2$, NHCOCH$_3$, cycloalkyl, heterocycloalkyl, heteroaryl, aryl and the like.

The term "cycloalkyl" as used herein refers to three to seven member cyclic hydrocarbon radicals. The cycloalkyl group optionally incorporates one or more double or triple bonds, or a combination of double or triple bonds, but which is not aromatic. Typical, non-limiting examples of cycloalkyl groups include cyclopropyl, cyclobutyl, cyclopentyl, cyclohexyl, and cycloheptyl. The cycloalkyl may be unsubstituted, or substituted with one or more substituents. Typical, non-limiting examples of such substituents include $C_1$-$C_6$ alkyl, halogen, alkoxy, CN, SH, COOH, COOC$_1$-C$_6$alkyl, CONH$_2$, OH, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like.

The term "aryl" as used herein refers to a monocyclic or polycyclic aromatic hydrocarbon. Typical, non-limiting examples of aryl groups include phenyl, naphthyl, anthracenyl, flourenyl, phenanthrenyl, indenyl and the like. The aryl group may be unsubstituted, or substituted with one or more substituents. Typical, non-limiting examples of such substituents include C1-C6 alkyl, halogen, alkoxy, CN, COOH, CONH$_2$, OH, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like. In some embodiments, the term "aryl" refers to a monocyclic or polycyclic aromatic hydrocarbon radical containing up to 14 ring atoms.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include pyridyl, pyrimidinyl, pyrazinyl, pyridazinyl, triazinyl, furanyl, pyrrolyl, thienyl, oxadiazolyl, thiadiazolyl, tetrazolyl, oxazolyl, thiazolyl, imidazolyl, pyrazolyl, triazonyl, isoxazolyl, oxadiazolyl, oxatriazolyl, isothiazolyl, thiatriazolyl, thiazinyl, oxazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-pyridazinyl, purinyl, benzofuranyl, isobenzofuranyl, benzothienyl, benzothiophenyl, carbazolyl, benzimidazolyl, benzoxazolyl, benzoisoxazolyl, benzothiazolyl, benzotriazolyl, indolyl, isoindolyl, quinolinyl, isoquinolinyl, acridinyl, naphthothienyl, thianthrenyl, chromenyl, xanthenyl, phenoxathienyl, indolizinyl, indazolyl, phthalazinyl, naphthyridinyl, qinoxalinyl, quinazolinyl, cinnolinyl, pteridinyl, beta-carbolinyl, phenanthridinyl, phenanthrolinyl, phenazinyl, phenothiazinyl, phenoxazinyl and the like. The heteroaryl group may be unsubstituted, or substituted with one or more substituents. Typical, non-limiting examples of such substituents include C1-C6 alkyl, halogen, alkoxy, CN, COOH, CONH$_2$, OH, SH, SCH$_3$, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like. In some embodiments, the term "heteroaryl" refers to a monocycle or polycyclic aromatic hydrocarbon radical containing up to 14 ring atoms.

The term "heterocycloalkyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting example of heterocycloalkyl groups include azetidinyl, pyrrolidinyl, 2-oxo-pyrrolidinyl, imidazolidin-2-one-yl, piperidinyl, oxazinyl, thiazinyl, piperazinyl, piperazin-2,3-dione-yl, morpholinyl, thiomorpholinyl, azepanyl, and the like. The heterocycloalkyl may be unsubstituted, or substituted with one or more substituents. Typical, non-limiting examples of such substituents include C$_1$-C$_6$ alkyl, halogen, alkoxy, CN, COOH, CONH$_2$, OH, NH$_2$, NHCOCH$_3$, heteroaryl, aryl, SO$_2$-alkyl, SO$_2$-aryl, OSO$_2$-aryl and the like.

The term "halogen" or halo as used herein refers to chlorine, bromine, fluorine or iodine.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

The term "optionally substituted" as used herein means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable derivative" as used herein refers to and includes any pharmaceutically acceptable salt, pro-drugs, metabolites, esters, ethers, hydrates, polymorphs, solvates, complexes or adducts of a compound described herein which, upon administration to a subject, is capable of providing (directly or indirectly) the parent compound. For example, the term "antibacterial or a pharmaceutically acceptable derivative thereof" includes all derivatives of the antibacterial agent (such as salt, prodrugs, metabolites, esters, ethers, hydrates, polymorphs, solvates, complexes or adducts) which, upon administration to a subject, is capable of providing (directly or indirectly) the antibacterial compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irrigation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutical acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional group capable of being converted into salt, each such functional group may be converted to salt independently. For example, in case of compounds containing two basic nitrogen atoms, one of the basic nitrogen can form salt with one acid while the other basic nitrogen can form salt with another acid. Some compounds according to the invention contain both acidic as well as basic moieties, and thus can form inner salts or corresponding zwitterions. In general, all pharmaceutically acceptable salt forms of compound of Formula (I) according to invention including acid addition salts, base addition salts, zwitterions or the like are contemplated to be within the scope of the present invention and are generically referred to as pharmaceutically acceptable salts.

The term "OBn" as used herein refers to benzyloxy.

The term "EDC" as used herein refers to 1-ethyl-3-(3-dimethylamino propyl)carbodiimide.

The term "HOBt" as used herein refers to 1-hydroxybenzotriazole.

The term "Boc" as used herein refers to tert-butyloxycarbonyl

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal floras, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection one or more symptoms of the bacterial infection, or (iii)

reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop or mouthwash. In case of a pharmaceutical composition comprising more than one ingredient (active or inert), one of the way of administering such composition is by admixing the ingredients (e.g. in the form of a suitable unit dosage form such as tablet, capsule, solution, powder or like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including the processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound either partially or completely, The term "beta-lactamase inhibitor" as used herein refers to a compound capable of inhibiting activity of one or more beta-lactamase enzymes, either partially or completely.

The term "Extended spectrum beta-lactamase or ESBL" as used herein includes those beta-lactamase enzymes which are capable of conferring bacterial resistance to the penicillins, first-, second-, and third-generation cephalosporins, and aztreonam by hydrolysis of these antibiotics.

The term "pharmaceutically inert ingredient" or "carrier" or "excipient" refers to a compound or material used to facilitate administration of a compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil peanut and sesame oils. In addition, various adjuvants commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, $8^{th}$ Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

In general, the term "cation" includes H, Na, K, Mg, Ca, $NH_4^+$, $(CH_3CH_2)_3N^+$ etc.

In one general aspect, there are provided compounds of Formula (I):

Formula (I)

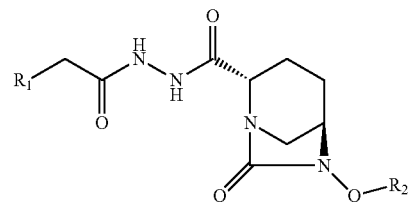

or a stereoisomer or a pharmaceutically acceptable derivative thereof;
wherein:
R₁ is:
(a) $C_1$-$C_6$ alkyl optionally substituted with one or more substituents independently selected from $C_1$-$C_6$ alkyl, halogen, CN, OR₃, NR₃R₄, CONR₃R₄, cycloalkyl, heterocycloalkyl, aryl, or heteroaryl;
(b) aryl optionally substituted with one or more substituents independently selected from $C_1$-$C_6$ alkyl, halogen, CN, OR₃, NR₃R₄, or CONR₃R₄, or
(c) heteroaryl optionally substituted with one or more substituents independently selected from $C_1$-$C_6$ alkyl, halogen, CN, OR₃, NR₃R₄, or CONR₃R₄;
R₂ is:
(a) SO₃M,
(b) CF₂COOM,
(c) CHFCOOM,
(d) CH₂COOM, or
(e) CF₃;
R₃ and R₄ are each independently:
(a) hydrogen, or
(b) $C_1$-$C_6$ alkyl optionally substituted with one or more substituents independently selected from halogen, CN, OH, O($C_1$-$C_6$ alkyl), NH($C_1$-$C_6$ alkyl), N($C_1$-$C_6$ alkyl)₂, CONH($C_1$-$C_6$ alkyl), CON($C_1$-$C_6$ alkyl)₂, cycloalkyl, heterocycloalkyl, aryl or heteroaryl;
M is hydrogen or a cation.

Typical non-limiting examples of compounds according to the invention include:

(2S,5R)-sulfuric acid mono-[2-(N'-(4-hydroxyphenyl-acetyl)-hydrazinocarbonyl)-7-oxo-1,6-diaza-bicyclo[3.2.1]oct-6-yl]ester;

(2S,5R)-sulfuric acid mono-[2-(N'-{2-[4-(2-aminoethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((R)-2-aminopropoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-(3-phenyl-propinoyl)-hydrazinocarbonyl)-7-oxo-1,6-diaza-bicylo[3.2.1]oct-6-yl]ester;

(2S,5R)-sulfuric acid mono-[2-(N'-(4-phenyl-butanoyl)-hydrazinocarbonyl)-7-oxo-1,6-diaza-bicylo[3.2.1]oct-6-yl]ester;

(2S,5R)-sulfuric acid mono-[2-(N'-(3,3-diphenyl-propionyl)-hydrazinocarbonyl)-7-oxo-1,6-diaza-bicyclo[3.2.1]oct-6-yl]ester;

(2S,5R)-sulfuric acid mono-[2-(N'-(4-chlorophenyl-acetyl)-hydrazinocarbonyl)-7-oxo-1,6-diaza-bicyclo[3.2.1]oct-6-yl]ester;

(2S,5R)-sulfuric acid mono-[2-(N'-(4-cyanophenyl-acetyl)-hydrazinocarbonyl)-7-oxo-1,6-diaza-bicyclo[3.2.1]oct-6-yl]ester;

(2S,5R)-sulfuric acid mono-[2-(N'-(4-aminophenyl-acetyl)-hydrazinocarbonyl)-7-oxo-1,6-diaza-bicyclo[3.2.1]oct-6-yl]ester;

(2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester;

(2S,5R)-sulfuric acid mono-[2-(N'-(4-N,N-dimethylaminophenyl-acetyl)-hydrazinocarbonyl)-7-oxo-1,6-diaza-bicyclo[3.2.1]oct-6-yl]ester;

(2S,5R)-sulfuric acid mono-[2-(N'-(4-methoxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(2-ethoxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(2-fluoro-4-ethoxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(4-amino-2-fluorophenyl-acetyl)-hydrazinocarbonyl)-7-oxo-1,6-diaza-bicyclo[3.2.1]oct-6-yl]ester;

(2S,5R)-sulfuric acid mono-[2-(N'-(2-fluoro-4-hydroxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(2-hydroxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(3-hydroxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(2-aminophenyl-acetyl)-hydrazinocarbonyl)-7-oxo-1,6-diaza-bicyclo[3.2.1]oct-6-yl]ester;

2,2-dimethyl-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(S)-2-amino-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(S)-2-amino-3-methyl-butyric acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(S)-pyrrolidine-2-carboxylic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(2S,5R)-malonic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;

(2S,5R)-succinic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;

(2S,5R)-cyclohexyl-carbamic acid 4-{2-oxo-2-[N'-(7-oxo-6-sulphooxy-1,6-diaza-bicyclo[3.2.1]octane-2-carbonyl)-hydrazino]ethyl}-phenyl ester;

3-methyl-2-(4-{2-oxo-2-[N'-(7-oxo-6-sulphooxy-1,6-diaza-bicyclo[3.2.1]octane-2-carbonyl)-hydrazino]-ethyl}-phenoxycarbonylamino)-butyric acid tert-butyl ester (S)-3-methyl-2-(4-{2-oxo-2-[N'-((2S,5R)-7-oxo-6-sulphooxy-1,6-diaza-bicyclo[3.2.1]-octane-2-carbonyl)-hydrazino]-ethyl}-phenoxycarbonylamino)-butyric acid tert-butyl ester;

(2S,5R)-sulfuric acid mono-[2-(N'-(2-fluoro-4-(2-aminoethoxy)-phenyl-acetyl)-hydrazinocarbonyl)-7-oxo-1,6-diaza-bicyclo[3.2.1]oct-6-yl]ester;

(2S,5R)-sulfuric acid mono-[2-(N'-{2-[3-(2-aminoethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-(2-hydroxyethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-(3-aminopropoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-(3-aminopropoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-(2-N-methylamino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-(2-N-methyl-amino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-(2-N-methyl-amino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-(2-N-methylamino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((R)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((R)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((R)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((S)-pyrrolidin-3-oxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((R)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((R)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((S)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((R)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((S)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((R)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((S)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((R)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((S)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((R)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((S)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((R)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((R)-pyrrolidin-3-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((S)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((R)-pyrrolidin-2-ylmethoxy)-phenyl]-acetyl}-hydrazinocarbonyl)-7-oxo-1,6-diaza-bicyclo[3.2.1] oct-6-yl]ester;

(2S,5R)-sulfuric acid mono-[2-(N'-{2-[2-((S)-pyrrolidin-3-oxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((S)-pyrrolidin-3-oxy)-phenyl]-acetyl}-hydrazinocarbonyl)-7-oxo-1,6-diaza-bicyclo[3.2.1] oct-6-yl. 1 ester;

isobutyric acid 1-[2-(2-{2-oxo-2-[N'-((2S,5R)-6-sulphooxy-7-oxo-1,6-diaza-bicyclo[3.2.1] octane-2-carbonyl)-hydrazino]-ethyl}-phenoxy)-ethylcarbamoyloxy]-ethyl ester.

or a stereoisomer or a pharmaceutically acceptable derivative thereof.

In some embodiments, typical non-limiting examples of compounds according to the invention include:

sodium salt of (2S,5R)-sulfuric acid mono-(2-(N'-(4-hydroxyphenyl-acetyl)-hydrazinocarbonyl)-7-oxo-1,6-diaza-bicyclo[3.2.1] oct-6-yl]ester;

sodium salt of (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-(3-phenyl-propinoyl)-hydrazinocarbonyl)-7-oxo-1,6-diaza-bicylo[3.2.1]oct-6-yl]ester;

sodium salt of (2S,5R)-sulfuric acid mono-[2-(N'-(4-phenyl-butanoyl)-hydrazinocarbonyl)-7-oxo-1,6-diaza-bicylo[3.2.1]oct-6-yl]ester;

sodium salt of (2S,5R)-sulfuric acid mono-[2-(N'-(3,3-diphenyl-propionyl)-hydrazinocarbonyl)-7-oxo-1,6-diaza-bicyclo[3.2.1]oct-6-yl]ester;

sodium salt of (2S,5R)-sulfuric acid mono-[2-(N'-(4-chlorophenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(4-cyanophenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(4-aminophenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(4-N,N-dimethylaminophenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(4-methoxyphenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(2-ethoxyphenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(2-fluoro-4-ethoxyphenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(4-amino-2-fluorophenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(2-fluoro-4-hydroxyphenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(2-hydroxyphenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(3-hydroxyphenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-(2-aminophenyl-acetyl)-hydrazinocarbonyl)-7-oxo-1,6-diaza-bicyclo[3.2.1]oct-6-yl]ester;

sodium salt of 2,2-dimethyl-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

sodium salt of (S)-2-amino-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

sodium salt of (S)-2-amino-3-methyl-butyric acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

sodium salt of (S)-pyrrolidine-2-carboxylic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

sodium salt of (2S,5R)-malonic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;

sodium salt of (2S,5R)-succinic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;

sodium salt of (2S,5R)-cyclohexyl-carbamic acid 4-{2-oxo-2-[N'-(7-oxo-6-sulphooxy-1,6-diaza-bicyclo[3.2.1]octane-2-carbonyl)-hydrazino]ethyl}-phenyl ester;

sodium salt of 3-methyl-2-(4-{2-oxo-2-[N'-(7-oxo-6-sulphooxy-1,6-diaza-bicyclo[3.2.1]octane-2-carbonyl)-hydrazino]-ethyl}-phenoxycarbonylamino)-butyric acid tert-butyl ester;

sodium salt of (S)-3-methyl-2-(4-{2-oxo-2-[N'-((2S,5R)-7-oxo-6-sulphooxy-1,6-diaza-bicyclo[3.2.1]-octane-2-carbonyl)-hydrazino]-ethyl}-phenoxycarbonylamino)-butyric acid tert-butyl ester;

sodium salt of (2S,5R)-sulfuric acid mono-[2-(N'-(2-fluoro-4-(2-amino-ethoxy)-phenyl-acetyl)-hydrazinocarbonyl)-7-oxo-1,6-diaza-bicyclo[3.2.1]oct-6-yl]ester;

sodium salt of (2S,5R)-sulfuric acid mono-[2-(N'-{2-[3-(2-amino-ethoxy)-phenyl]-acetyl}-hydrazinocarbonyl)-7-oxo-1,6-diaza-bicyclo[3.2.1]oct-6-yl]ester;

sodium salt of (2S,5R)-Sulfuric acid mono-[2-(N'-{2-[2-(2-hydroxy-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-(3-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-(3-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-(2-N-methylamino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-(2-N-methylamino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-(2-N-methylamino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-(2-N-methylamino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((S)-pyrrolidin-3-oxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((S)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((R)-pyrrolidin-2-ylmethoxy)-phenyl]acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((S)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-pyrrolidin-3-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-pyrrolidin-3-oxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-pyrrolidin-3-oxy)-phenyl]-acetyl}-hydrazinocarbonyl)-7-oxo-1,6-diaza-bicyclo[3.2.1]oct-6-yl]ester;

sodium salt of isobutyric acid 1-[2-(2-{2-oxo-2-[N'-((2S,5R)-6-sulphooxy-7-oxo-1,6-diaza-bicyclo[3.2.1]octane-2-carbonyl)-hydrazino]-ethyl}-phenoxy)-ethylcarbamoyloxy]-ethyl ester.

or a stereoisomer thereof.

In general, the compounds of the invention can be prepared according to the general procedures given in Schemes 1 and 2. A person of skills in the art would appreciate that the described method can be varied or optimized further to provide the desired and related compounds. In the following procedures, all variables are as defined above.

In some embodiments, there is provided a process for preparation of compounds of Formula (I):

Formula (I)

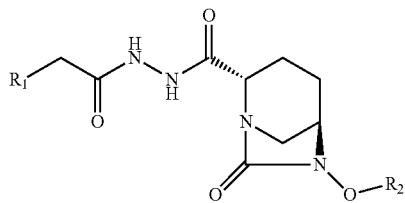

or a stereoisomer or a pharmaceutically acceptable derivative thereof;
wherein
$R_1$ is:
(a) $C_1$-$C_6$ alkyl optionally substituted with one or more substituents independently selected from $C_1$-$C_6$ alkyl, halogen, CN, $OR_3$, $NR_3R_4$, $CONR_3R_4$, cycloalkyl, heterocycloalkyl, aryl, or heteroaryl;
(b) aryl optionally substituted with one or more substituents independently selected from $C_1$-$C_6$ alkyl, halogen, CN, $OR_3$, $NR_3R_4$, or $CONR_3R_4$, or (c) heteroaryl optionally substituted with one or more substituents independently selected from $C_1$-$C_6$ alkyl, halogen, CN, $OR_3$, $NR_3R_4$, or $CONR_3R_4$;

$R_2$ is —$SO_3M$;

$R_3$ and $R_4$ are each independently:

(a) hydrogen, or (b) $C_1$-$C_6$ alkyl optionally substituted with one or more substitutents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ CON($C_1$-$C_6$ alkyl)$_2$, cycloalkyl, heterocycloalkyl, aryl or heteroaryl;

M is hydrogen or a cation;

said process comprising:

(a) reacting a compound of Formula (Ia) with $R_1CONHNH_2$(Ib) in presence of coupling agent to obtain a compound of Formula (Ic);

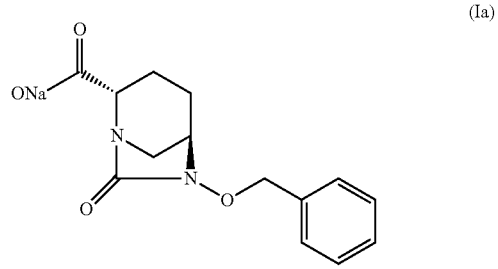

(Ia)

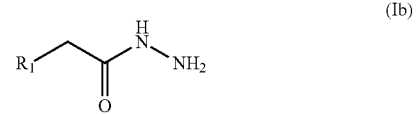

(Ib)

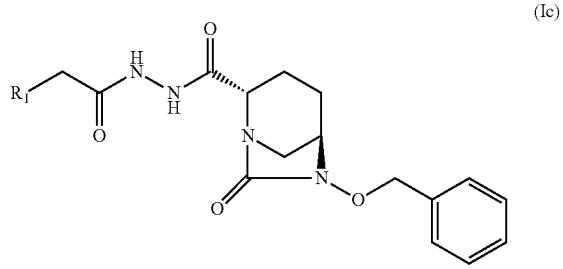

(Ic)

(b) hydrogenolysis of a compound of Formula (Ic) to obtain a compound of Formula (Id);

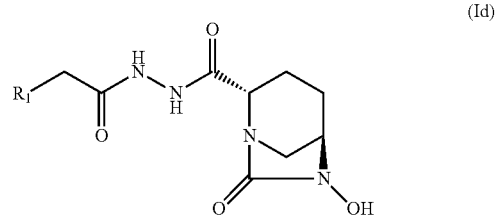

(Id)

(c) sulfonating a compound of Formula (Id), followed by the treatment with tetrabutyl ammonium hydrogen sulfate to obtain a compound of Formula (Ie); and

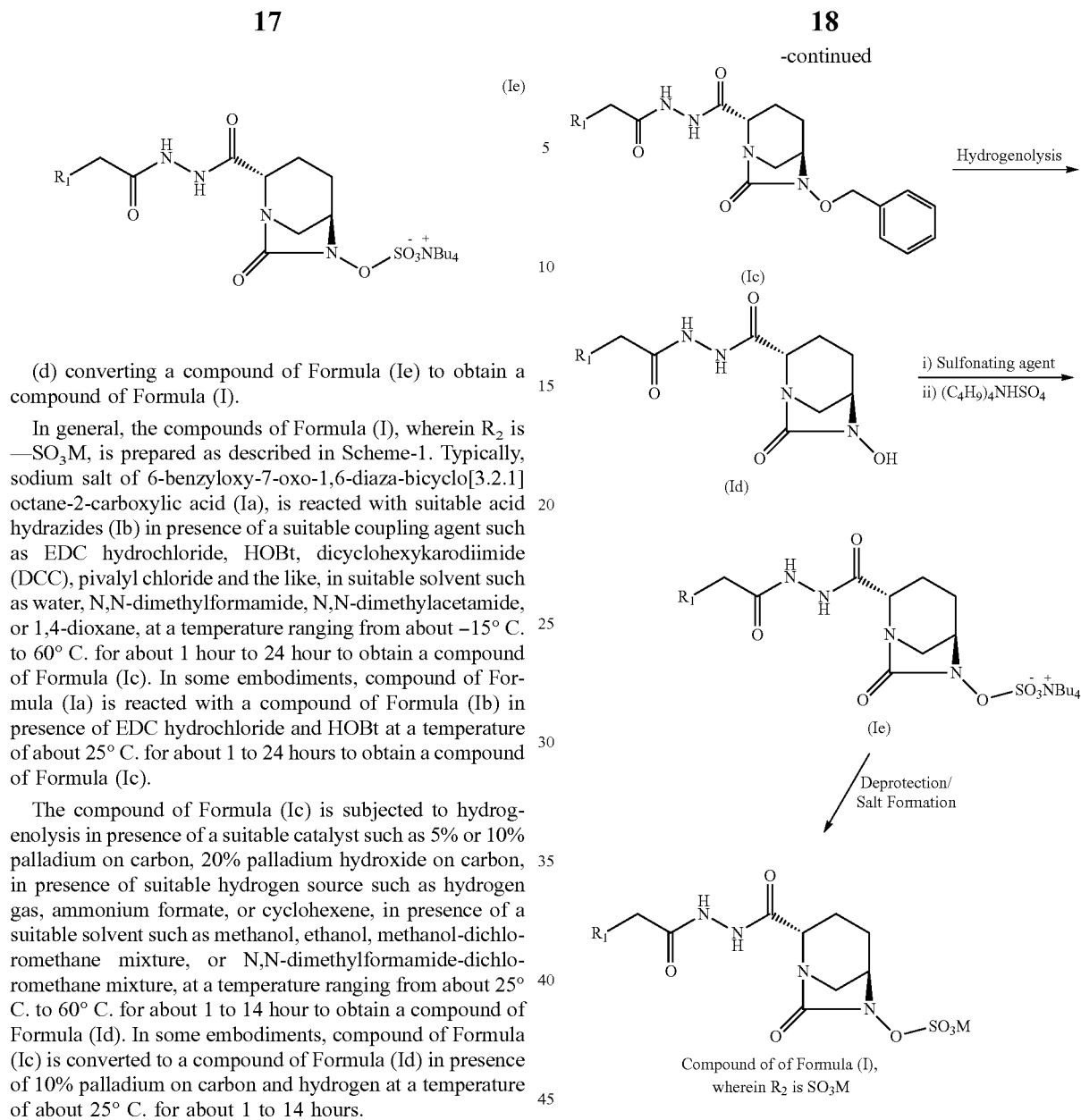

(d) converting a compound of Formula (Ie) to obtain a compound of Formula (I).

In general, the compounds of Formula (I), wherein $R_2$ is —$SO_3M$, is prepared as described in Scheme-1. Typically, sodium salt of 6-benzyloxy-7-oxo-1,6-diaza-bicyclo[3.2.1] octane-2-carboxylic acid (Ia), is reacted with suitable acid hydrazides (Ib) in presence of a suitable coupling agent such as EDC hydrochloride, HOBt, dicyclohexykarodiimide (DCC), pivalyl chloride and the like, in suitable solvent such as water, N,N-dimethylformamide, N,N-dimethylacetamide, or 1,4-dioxane, at a temperature ranging from about −15° C. to 60° C. for about 1 hour to 24 hour to obtain a compound of Formula (Ic). In some embodiments, compound of Formula (Ia) is reacted with a compound of Formula (Ib) in presence of EDC hydrochloride and HOBt at a temperature of about 25° C. for about 1 to 24 hours to obtain a compound of Formula (Ic).

The compound of Formula (Ic) is subjected to hydrogenolysis in presence of a suitable catalyst such as 5% or 10% palladium on carbon, 20% palladium hydroxide on carbon, in presence of suitable hydrogen source such as hydrogen gas, ammonium formate, or cyclohexene, in presence of a suitable solvent such as methanol, ethanol, methanol-dichloromethane mixture, or N,N-dimethylformamide-dichloromethane mixture, at a temperature ranging from about 25° C. to 60° C. for about 1 to 14 hour to obtain a compound of Formula (Id). In some embodiments, compound of Formula (Ic) is converted to a compound of Formula (Id) in presence of 10% palladium on carbon and hydrogen at a temperature of about 25° C. for about 1 to 14 hours.

The compound of Formula (Id) is sulfonated by reacting with a suitable sulfonating reagent such as sulfur trioxide-pyridine complex, or sulfur trioxide-N,N-dimethylformamide complex, in presence of a suitable solvent such as pyridine, or N,N-dimethyl formamide, at a temperature ranging from about 25° C. to 90° C. for about 1 to 24 hours to obtain corresponding pyridine salt of sulfonic acid. This is further treated with suitable reagent such as tetrabutylammonium acetate, tetrabutylammonium hydrogen sulfate, tetrabutylammonium sulfate and the like to provide tetrabutylammonium salt of sulfonic acid as a compound of Formula (Ie). In some embodiments, compound of Formula (Id) is sulfonated in presence of sulfur trioxide-pyridine complex at a temperature of about 25° C. for about 1 to 24 hours. The sulphonated compound is further treated with tetrabutylammonium hydrogen sulfate to provide a compound of Formula (Ie).

Some compounds according to invention are isolated as zwitterions, by treating a compound of Formula (Ie) with Scheme-1

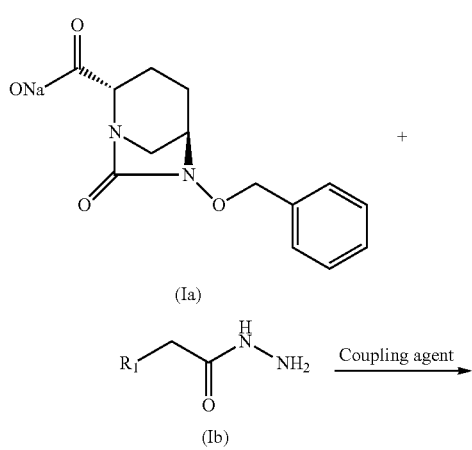

trifluoroacetic acid, in a suitable solvent such as dichloromethane, chloroform, or acetonitrile, at a temperature ranging from about −15° C. to 40° C. for about 0.5 to 14 hours. In some embodiments, compound of Formula (Ie) is treated with trifluoroacetic acid in presence of dichloromethane at a temperature of about −10° C. for about 0.5 to 14 hours hour to obtain a compound of Formula (I), wherein $R_2$ is —$SO_3M$.

Some other compounds according to the invention are isolated as a corresponding sodium salt, by passing intermediate compound of Formula (Ie) through sodium form of Amberlite 200C resin in a tetrahydrofuran-water mixture followed by evaporation of the solvent under vacuum.

The compounds according to invention wherein $R_2$ is selected from $CF_2COOM$ or $CHFCOOM$ or $CH_2COOM$ were prepared by general reaction scheme as described in Scheme-2. The hydroxyl intermediate (Id) obtained as per Scheme-1, is subjected to alkylation with an alkylating agent (IIa) such as ethyl-bromoacetate, ethyl-bromofluoroacetate, or ethyl-bromodifluoroacetate, in presence of a base such as potassium carbonate, diisopropylethylamine or triethylamine, in a suitable solvent such as N,N-dimethyl formamide, N,N-dimethylacetamide or N-methyl pyrrolidine, to provide O-alkylated compound (IIb).

The compound of Formula (IIb) is subjected for hydrolysis in presence of a base such as lithium hydroxide or potassium hydroxide, in a suitable solvent such as aqueous tetrahydrofuran or aqueous dioxane, to provide compound of Formula (I). Optionally, if $R_1$ bears amine function protected with Boc group, then it is removed with an additional step of deprotection by using a suitable deprotecting agent (such as trifluoroacetic acid or hydrogen fluoride-pyridine) in a suitable solvent such as dichloromethane, chloroform or acetonitrile, to provide a compound of Formula (I), wherein, $R_2$ is selected from $CF_2COOM$ or $CHFCOOM$ or $CH_2COOM$.

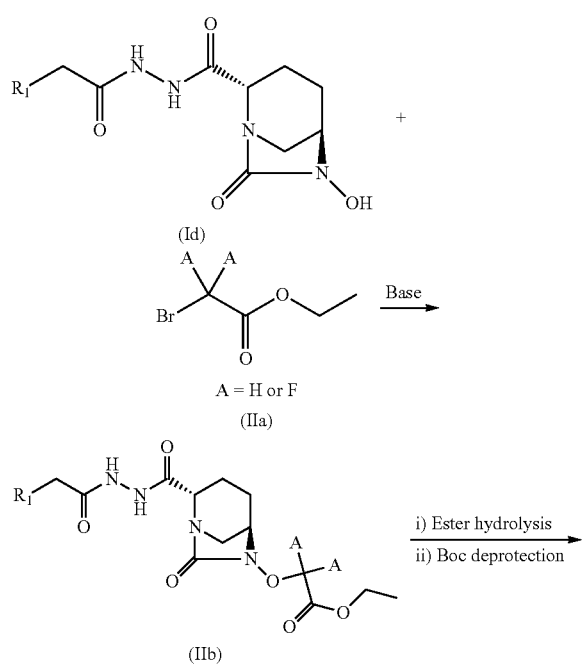

Scheme-2

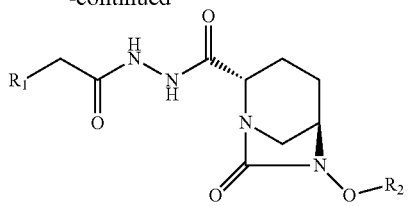

Compound of Formula (I), wherein
$R_2$ is ——$CA_2COOH$ and A is H or F

In some embodiments, there are provided pharmaceutical compositions comprising a compound of Formula (I) or a stereoisomer or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) a compound of Formula (I) or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising a compound of Formula (I) or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical, composition comprising: (a) a compound of Formula (I) or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject a compound of Formula (I) or a stereoisomer or a pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, there are provided pharmaceutical compositions comprising (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof.

In some other embodiments, there are provided pharmaceutical compositions comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl] ester or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl] ester or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl] ester or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl] ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl] ester or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl] ester or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, there are provided pharmaceutical compositions comprising (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof.

In some other embodiments, there are provided pharmaceutical compositions comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]

oct-6-yl]ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1] oct-6-yl]ester or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, there are provided pharmaceutical compositions comprising (2S,5R)-sulfuric acid mono-[2-(N'-(4-amino methyl-phenyl-acetyl)-hydrazinocarbonyl)-7- oxo-1,6-diaza-bicyclo[3.2.1]oct-6-yl]ester or a stereoisomer or a pharmaceutically acceptable derivative thereof.

In some other embodiments, there are provided pharmaceutical compositions comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a(2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl] ester or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl] ester or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl] ester or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl] ester or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl] ester or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl] ester or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester or a stereoisomer or a pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-(4-amino methyl-phenyl-acetyl)-hydrazinocarbonyl)-7-oxo-1,6-diaza-bicyclo[3.2.1] oct-6-yl]ester or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-(4-amino methyl-phenyl-acetyl)-hydrazinocarbonyl)-7-oxo-1,6-diaza-bicyclo[3.2.1] oct-6-yl]ester or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-(4-amino methyl-phenyl-acetyl)-hydrazinocarbonyl)-7-oxo-1,6-diaza-bicyclo[3.2.1] oct-6-yl]ester or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-(4-amino methyl-phenyl-acetyl)-hydrazinocarbonyl)-7-oxo-1,6-diaza-bicyclo[3.2.1] oct-6-yl]ester or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) (2S,5R)-sulfuric acid mono-[2-(N'-(4-amino methyl-phenyl-acetyl)-hydrazinocarbonyl)-7-oxo-1,6-diaza-bicyclo[3.2.1] oct-6-yl]ester or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, the compositions and methods according to the invention use compounds of Formula (I), or a stereoisomer, or a pharmaceutically acceptable derivative thereof, in combination with at least one antibacterial agent. A wide variety of antibacterial agents can be used. Typical, non-limiting examples of antibacterial agents include one or more of antibacterial compounds generally classified as aminoglycosides, ansamycins, carbacephems, cephalosporins, cephamycins, lincosamides, lipopeptides, macrolides, monobactams, nitrofurans, penicillins, polypeptides, quinolones, sulfonamides, tetracyclines, oxazolidinone and the like. Typical, non-limiting examples of aminoglycoside antibacterial agents include amikacin, gentamicin, kanamycin, neomycin, netilmicin, tobramycin, paromomycin, arbekacin, streptomycin, apramycin and the like. Typical, non-limiting examples of ansamycin antibacterial agents include geldanamycin, herbimycin and the like. Typical, non-limiting examples of carbacephem antibacterial agents include loracarbef and the like. Typical, non-limiting examples of carbapenam antibacterial agents include ertapenem, doripenem, imipenem, meropencm and the like.

Typical, non-limiting examples of cephalosporin and cephamycin antibacterial agents include cefazolin, cefacetrile, cefadroxil, cefalexin, cefaloglycin, ccfalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cethuperazone, cefuroxime, cefuzonam, cephamycin, cefoxitin, cefotetan, cefmetazole, carbacephem, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, cefiolene, ceftizoxime, oxacephem, cefepime, cefozopran, cefpirome, cefquinome, ceftobiprole, cetiofur, cefquinome, cefovecin, CXA-101, ceftaroline, ceftobiprole, cefoselis, cefluprenam, cefclidin, loracarbacef, ceftolozane, latamoxef and the like.

Typical, non-limiting examples of lincosamide antibacterial agents include clindamycin, lincomycin and the like. Typical, non-limiting examples of macrolide antibacterial agents include azithromycin, clarithromycin, dirithromycin, erythromycin, roxithromycin, troleandomycin, telithromycin, spectinomycin and the like. Typical, non-limiting examples of monobactam antibacterial agents include aztreonam and the like. Typical, non-limiting examples of nitrofuran antibacterial agents include furazolidone, nitrofurantoin and the like. Typical, non-limiting examples of penicillin antibacterial agents include amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, colistin, polymyxin B and the like.

Typical, non-limiting examples of polypeptide antibacterial agents include bacitracin, colistin, polymyxin B and the like. Typical, non-limiting examples of quinolone antibacterial agents include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin and the like. Typical, non-limiting examples of sulfonamide antibacterial agents include mafenide, sulfonamidochrysoidine, sulfacetamide, sulfadiazine, sulfamethizole, sulfamethoxazole, sulfasalazine, sulfisoxazole, trimethoprim and the like. Typical, non-limiting examples of tetracycline antibacterial agents include demeclocycline, doxycycline, minocycline, oxytetracycline, tetracycline, tigecycline and the like. Typical non-limiting examples of oxazolidinone anti-bacterial agents include linezolid, ranbezolid, torezolid, radezolid and the like. Typical non-limiting examples of beta-lactamase inhibitor include sulbactam, tazobactam, clavulanic acid, avibactam and the like.

The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, preservatives, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for oral or parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and the nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, compounds and compositions according to invention are administered orally or parenterally.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered separately, the invention further provides for combining separate pharmaceutical compositions in kit form. The kit may comprise one or more separate pharmaceutical compositions, each comprising one or more active ingredients. Each of such separate compositions may be present in a separate container such as bottle, vial, syringes, boxes, bags, and the like. Typically, the kit comprises directions for the administration of the separate components. The kit form is particularly advantageous when the separate components are preferably administered in different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, pharmaceutical compositions and methods according to the invention are used in treatment or prevention of infections caused by resistant bacteria. The compounds, compositions and methods according to the invention are also used in treatment or prevention of infections caused by bacteria producing one or more beta-lactamase enzymes including those belonging to extended spectrum beta-lactamase enzymes.

In some embodiments, there is provided a method for preventing or treating a bacterial infection in a subject, said infection being caused by bacteria producing one or more beta-lactamase enzymes, wherein the method comprises administering to said subject a compound of Formula (I). In some other embodiments, there is provided a method for preventing or treating a bacterial infection in a subject, said infection being caused by bacteria producing one or more beta-lactamase enzymes, wherein the method comprises administering to said subject a pharmaceutical composition comprising compound of Formula (I).

In general, the compounds of Formula (I) or a stereoisomer or pharmaceutically acceptable derivative thereof according to invention are also useful in increasing antibacterial effectiveness of an antibacterial agent in a subject. The antibacterial effectiveness of one or more antibacterial agents may be increased, for example, by co-administering said antibacterial agents or a pharmaceutically acceptable derivative thereof with a compound of Formula (I) or a stereoisomer or a pharmaceutically acceptable derivative thereof according to the invention. In some embodiments, there are provided methods for increasing antibacterial effectiveness of an antibacterial agent in a subject, said method comprising co-administering said antibacterial agent or a pharmaceutically acceptable derivative thereof with a compound of Formula (I), or a stereoisomer, or a pharmaceutically acceptable derivative thereof.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1

Sodium Salt of (2S,5R)-Sulfuric Acid mono-[2-(N'-(4-hydroxyphenyl-acetyl)-hydrazinocarbonyl)-7-oxo-1,6-diaza-bicyclo[3.2.1]oct-6-yl]ester

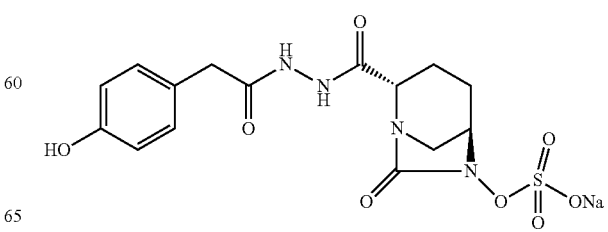

Step-1: Preparation of (2S,5R)-2-(N'-(4-tert-butyldimethylsilyloxy-phenyl-acetyl)-hydrazinocarbonyl)-7-oxo-6-benzyloxy-1,6-diaza-bicyclo[3.2.1]octane To the suspension of sodium (2S,5R)-7-oxo-6-benzyloxy-1,6-diaza-bicyclo[3.2.1]octane-2-carboxylate (35 g, 117.44 mmol) in a mixture of water (600 ml) and N,N-dimethylformamide (50 ml), was added 4-tert-butyldimethylsilyloxy-phenyl-acetic acid hydrazide (30 g, 107 mmol). To the reaction mixture, was added EDC hydrochloride (31.1 g, 160 mmol) followed by hydroxybenzotriazole (14.5 g, 107 mmol) at 25° C. to 35° C. The suspension was stirred for 15 hours. The solid was filtered under suction and dried to provide a crude solid in 49.2 g quantity, which was further purified by silica gel column chromatography to furnish 31.2 g of (2S,5R)-2-(N'-(4-tert-butyldimethylsilyloxy-phenyl-acetyl)-hydrazinocarbonyl)-7-oxo-6-benzyloxy-1,6-diaza-bicyclo[3.2.1] octane as a solid in 49% yield.

Analysis:
Mass: 537.5 (M−1), for Molecular Formula of $C_{28}H_{38}N_4O_5Si$;
$^1H$ NMR: (DMSO-d6): δ 9.99 (s, 1H), 9.94 (s, 1H), 7.32-7.44 (m, 5H), 7.14 (d, 2H), 6.75 (d, 2H), 4.92 (d, 2H), 3.80 (d, 1H), 3.67 (s, 1H), 3.36 (s, 2H), 3.21 (d, 1H), 2.87 (d, 1H), 1.97-2.03 (m, 1H), 1.90-1.95 (m, 1H), 1.58-1.88 (m, 2H), 0.92 (s, 9H), 0.15 (s, 6H).

Step-2: Preparation of (2S,5R)-2-(N'-(4-tert-butyldimethylsilyloxy-phenyl-acetyl)-hydrazinocarbonyl)-7-oxo-6-hydroxy-1,6-diaza-bicyclo[3.2.1]octane The clear solution of (2S,5R)-2-(N'-(4-tert-butyldimethylsilyloxy-phenyl-acetyl)-hydrazinocarbonyl)-7-oxo-6-benzyloxy-1,6-diaza-bicyclo[3.2.1]octane (30 g, 55.76 mmol) in methanol (300 ml), was subjected for catalytic hydrogenolysis by using 10% palladium on carbon (3.0 g) under atmospheric hydrogen gas pressure for 1.5 hour at 25° C. to 35° C. The suspension was filtered through celite bed and was washed with methanol (100 ml). The filtrate was evaporated below 40° C. using vacuum, to provide 25 g of (2S,5R)-2-(N'-(4-tert-butyldimethylsilyloxy-phenyl-acetyl)-hydrazinocarbonyl)-7-oxo-6-hydroxy-1,6-diaza-bicyclo[3.2.1]octane intermediate as a solid, which was used immediately for the next reaction.

Analysis:
Mass: 447.5 (M−1), for Molecular Formula of $C_{21}H_{32}N_4O_5Si$;
$^1H$ NMR: (DMSO-d6) δ 9.75 (br s, 3H), 7.15 (d, 2H), 6.75 (d, 2H), 3.76 (d, 1H), 3.58 (s, 1H), 3.37 (s, 2H), 3.18 (d, 1H), 2.96 (d, 1H), 1.99-2.05 (m, 1H), 1.81-1.94 (m, 1H), 1.70-1.79 (m, 1H), 1.54-1.62 (m, 1H), 0.93 (s, 9H), 0.15 (s, 6H).

Step-3: Preparation of Tetrabutyl Ammonium Salt of (2S,5R)-2-(N'-(4-tert-butyldimethylsilyloxy-phenyl-acetyl)-hydrazinocarbonyl)-7-oxo-6-sulphooxy-1,6-diaza-bicyclo[3.2.1]octane To the solution of (2S,5R)-2-(N'-(4-tert-butyldimethylsilyloxy-phenyl-acetyl)-hydrazinocarbonyl)-7-oxo-6-hydroxy-1,6-diaza-bicyclo[3.2.1]octane (25 gm, 55 mmol) as obtained in step-2, in dichloromethane (250 ml) was charged triethylamine (23.3 ml, 167.4 mmol) followed by sulfur trioxide pyridine complex (17.74 gm, 111.6 mmol) at 25° C. to 35° C. The clear solution was stirred for 3.5 hour. To the reaction mixture was added ethyl acetate (500 ml) and was quenched by adding 0.5 N aqueous potassium dihydrogen othrophosphate solution (850 ml). Layers were separated and aqueous layer was washed with ethyl acetate (100 ml). To the aqueous layer was added tetrabutylammonium hydrogen sulfate (17.05 gm, 50 mmol) and it was stirred for 2 hour. The mixture was extracted with dichloromethane (500 ml×2). Combined organic layer was washed with brine and evaporated under vacuum to provide crude mass which was purified by silica gel column chromatography to yield 32 g of tetra-butyl ammonium salt of (2S,5R)-2-(N'-(4-tert-butyldimethylsilyloxy-phenyl-acetyl)-hydrazinocarbonyl)-7-oxo-6-hydroxy-1,6-diaza-bicyclo[3.2.1] octane intermediate as solid in 74% yield.

Analysis:
Mass: 527.4 (M−1) as a free sulfonic acid, for Molecular Formula of $C_{21}H_{31}N_4O_8SSi$. $N(C_4H_9)_4$.
$^1H$ NMR (CDCl$_3$): δ 8.53 (d, 1H), 7.46 (d, 1H), 7.16 (d, 2H), 6.82 (d, 2H), 4.33 (s. 1H), 3.96 (d, 1H), 3.59 (s, 2H), 3.36 (d, 1H), 3.26-3.30 (m, 8H), 3.11 (d, 1H), 2.30-2.36 (m, 1H), 2.16-2.21 (m, 1H), 1.83-1.93 (m, 2H), 1.61-1.68 (m, 8H), 1.37-1.49 (m, 8H), 0.99 (s, 9H), 0.95-0.98 (m, 12H), 0.19 (s, 6H).

Step-4: Preparation of Tetrabutyl Ammonium Salt of (2S,5R)-2-(N'-(4-hydroxy-phenyl-acetyl)-hydrazinocarbonyl)-7-oxo-6-sulphooxy-1,6-diaza-bicyclo[3.2.1]octane To the solution of tetra-butyl ammonium salt of (2S,5R)-2-(N'-(4-tert-butyldimethylsilyloxy-phenyl-acetyl)-hydrazinocarbonyl)-7-oxo-6-sulphooxy-1,6-diaza-bicyclo[3.2.1]octane (8 g, 10 mmol) in tetrahydrofuran (80 ml) was added 1M solution of tetrabutylammonium fluoride in tetrahydrofuran (22 ml, 21.8 mmol) at 25° C. to 35° C. The reaction mixture was stirred for 2 hours. Reaction was quenched by addition of water (50 ml) and was diluted with ethyl acetate (100 ml). Aqueous layer was washed with ethyl acetate (100 ml). Combined organic layer was dried over sodium sulfate. It was evaporated under vacuum below 40° C. to provide 6.2 g of tetrabutyl ammonium salt of (2S,5R)-2-(N'-(4-hydroxy-phenyl-acetyl)-hydrazinocarbonyl)-7-oxo-6-sulphooxy-1,6-diaza-bicyclo[3.2.1]octane in 91% yield, which was used without further purification for the next step.

Analysis:
Mass: 413.3 (M−1) as a free sulfonic acid, for Molecular Formula of $C_{15}H_{18}N_4O_8S$. $N(C_4H_9)_4$.

Step-5: Sodium Salt of (2S,5R)-Sulfuric Acid mono-[2-(N'-(4-hydroxyphenyl-acetyl)-hydrazinocarbonyl)-7-oxo-1,6-diaza-bicyclo[3.2.1]oct-6-yl]ester Tetrabutyl ammonium salt of (2S,5R)-2-(N'-(4-hydroxyphenyl-acetyl)-hydrazinocarbonyl)-7-oxo-6-sulphooxy-1,6-diaza-bicyclo[3.2.1]octane (6.2 g 13.6 mmol) was dissolved in a mixture of tetrahydrofuran (4 ml) and water (3 ml). The clear solution was loaded on a column packed with activated Amberlite IR 120 Na resin. The column was eluted with 10% tetrahydrofuran in water. Fraction containing compound were collected and evaporated under reduced pressure below 40° C. to remove tetrahydrofuran. The remaining aqueous layer was extracted with dichloromethane (50 ml×2). The aqueous layer was evaporated to dryness under vacuum below 40° C. to provide a residue. The residue was triturated with acetone to provide 3.2 g of sodium salt of (2S,5R)-sulfuric acid mono-[2-(N'-(4-hydroxyphenylacetyl)-hydrazinocarbonyl)-7-oxo-1,6-diaza-bicyclo[3.2.1] oct-6-yl]ester as a solid, in 77% yield.

Analysis:

Mass: 413.2 (M−1) as free sulfonic acid; for Molecular Formula $C_{15}H_{17}N_4O_8SNa$;

$^1$H NMR (DMSO-d6): δ 9.88 (s, 1H), 9.83 (s, 1H), 9.20 (s, 1H), 7.06 (d, 2H), 6.66 (d, 2H), 3.97 (s, 1H), 3.78 (d, 1H), 3.20-3.30 (m, 3H), 2.96 (d, 1H), 1.97-2.02 (m, 1H), 1.82-1.96 (m, 1H), 1.57-1.72 (m, 2H).

Example-2

(2S,5R)-Sulfuric Acid mono-[2-(N'-{2-[2-(2-amino-ethoxy)-phenyl]-acetyl}-hydrazinocarbonyl)-7-oxo-1,6-diaza-bicyclo[3.2.1]oct-6-yl]ester

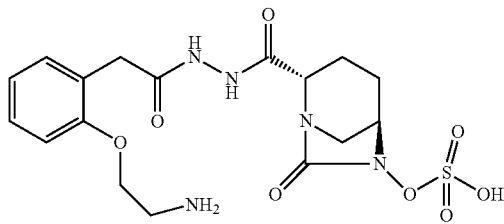 [SMILES: NCCOc1ccccc1CC(=O)NNC(=O)[C@@H]1CC[C@@H]2CN1C(=O)N2OS(=O)(=O)O]

Step-1: Preparation of (2S,5R)-2-(N'-{2-[2-(2-N-tert-butoxycarbonylamino-ethoxy)-phenyl]-acetyl}-hydrazinocarbonyl)-7-oxo-6-benzyloxy-1,6-diaza-bicyclo[3.2.1]octane To the suspension of sodium (2S,5R)-7-oxo-6-benzyloxy-1,6-diaza-bicyclo[3.2.1]octane-2-carboxylate (23 gm, 77.18 mmol) in N,N-dimethylformamide (230 ml), was added N,N-diisopropylethylamine (16.1 ml, 92.60 mmol) at 25° C. to 35° C. To the reaction mixture, was added EDC hydrochloride (22 g, 115.78 mmol) followed by 2-(N-tert-butoxycarbonylamino-ethoxy)-phenylacetic acid hydrazide (28.7 g, 92.88 mmol) and hydroxybenzotriazole (10.5 g, 77.77 mmol). The suspension was stirred for 15 hours. To the reaction mixture was charged water (1200 ml) and was extracted with diethyl ether (500 ml×3). Combined organic layer was washed with water followed by brine solution. It was evaporated under vacuum to provide crude product which was purified by silica gel column chromatography to furnish 42 g of (2S,5R)-2-(N'-{2-[2-(2-N-tert-butoxycarbonylamino-ethoxy)-phenyl]-acetyl}-hydrazinocarbonyl)-7-oxo-6-benzyloxy-1,6-diaza-bicyclo[3.2.1]octane as a solid in 88% yield.

Analysis:

Mass: 568.4 (M+1), for Molecular Formula of $C_{29}H_{37}N_5O_7$.

$^1$H NMR (CDCl3): δ 8.60-8.80 (br s, 2H), 7.35-7.41 (m, 5H), 7.22-7.26 (m, 2H), 6.94 (t, 1H), 6.84 (d, 1H), 5.30-5.40 (br s, 1H), 5.05 (d, 1H), 4.90 (d, 1H), 4.0-4.10 (m, 3H), 3.58-3.62 (m, 1H), 3.54 (s, 2H), 3.25-3.32 (m, 2H), 3.09 (d, 1H), 2.31-2.40 (m, 1H), 1.87-2.03 (m, 4H), 1.44 (s, 9H).

Step-2: Preparation of (2S,5R)-2-(N'-{2-[2-(2-N-tert-butoxycarbonylamino-ethoxy)-phenyl]-acetyl}-hydrazinocarbonyl)-7-oxo-6-hydroxy-1,6-diaza-bicyclo[3.2.1]octane The solution of (2S,5R)-2-(N'-{2-[2-(2-N-tert-butoxycarbonylamino-ethoxy)-phenyl]-acetyl}-hydrazinocarbonyl)-7-oxo-6-benzyloxy-1,6-diaza-bicyclo[3.2.1]octane (42 g, 74.07 mmol) as obtained in step-1, in methanol (210 ml), was subjected for catalytic hydrogenolysis by using 10% palladium on carbon (8.2 gm) under 60 psi hydrogen gas pressure for 1.5 hours at 25° C. to 35° C. The suspension was filtered through celite bed and was washed with methanol (200 ml). The filtrate was evaporated below 40° C. using vacuum. The obtained crude mass was stirred in diethyl ether (200 ml) and filtered to provide 29 g of (2S,5R)-2-(N'-{2-[2-(2-N-tert-butoxycarbonylamino-ethoxy)-phenyl]-acetyl}-hydrazinocarbonyl)-7-oxo-6-hydroxy-1,6-diaza-bicyclo[3.2.1]octane intermediate as a solid in 82% yield, which was used immediately for the next reaction.

Analysis:

Mass: 478.4 (M+1), for Molecular Formula of $C_{22}H_{31}N_5O_7$.

$^1$H NMR: (DMSO-d6) δ 9.82 (s, 1H), 9.72 (s, 1H), 8.29 (s, 1H), 7.23 (d, 1H), 7.18 (t, 1H), 6.98-6.99 (m, 1H), 6.84-7.00 (m, 2H), 3.89 (br s, 2H), 3.77 (d, 1H), 3.56 (s, 1H), 3.42 (s, 2H), 3.28-3.39 (m, 2H), 3.19 (d, 1H), 3.96 (d, 1H), 2.00-2.06 (m, 1H), 1.86-1.89 (m, 1H), 1.75-1.79 (m, 1H), 1.58-1.62 (m, 1H), 1.37 (s, 9H).

Step-3: Preparation of Tetrabutyl Ammonium Salt of (2S,5R)-2-(N'-{2-[2-(2-N-tert-butoxycarbonylamino-ethoxy)-phenyl]-acetyl}-hydrazinocarbonyl)-7-oxo-6-sulphooxy-1,6-diaza-bicyclo[3.2.1]octane To the solution of (2S,5R)-2-(N'-{2-[2-(2-N-tert-butoxycarbonylamino-ethoxy)-phenyl]-acetyl}-hydrazinocarbonyl)-7-oxo-6-hydroxy-1,6-diaza-bicyclo[3.2.1]octane (29 g, 60.79 mmol) as obtained in step-2, in dichloromethane (290 ml) was charged triethylamine (25.4 ml, 182.57 mmol) followed by sulfur trioxide pyridine complex (14.5 g, 91.10 mmol) at 25° C. to 35° C. The clear solution was stirred for 4 hours. To the reaction mixture was added ethyl acetate (580 ml) and was quenched by adding 1M aqueous potassium dihydrogenothrophosphate solution (580 ml). Layers were separated and aqueous layer was washed with ethyl acetate (290 ml×2). To the aqueous layer was added tetra butylammonium hydrogen sulfate (21.67 g, 63.82 mmol) and it was stirred for 15 hours. The mixture was extracted with dichloromethane (290 ml×2). Combined organic layer was washed with brine and evaporated under vacuum to provide crude mass which was purified by silica gel column chromatography to yield 40 g tetrabutylammonium salt of (2S,5R)-2-(N'-{2-[2-(2-N-tert-butoxycarbonylamino-ethoxy)-phenyl]-acetyl}-hydrazinocarbonyl)-7-oxo-6-sulphooxy-1,6-diaza-bicyclo[3.2.1]octane intermediate as a solid in 82% yield.

Analysis:

Mass: 556.3 (M−1) as a free sulfonic acid, for Molecular Formula of $C_{22}H_{30}N_5O_{10}S.N(C_4H_9)_4$.

Step-4: Preparation of (2S,5R)-Sulfuric Acid mono-[2-(N'-{2-[2-(2-amino-ethoxy)-phenyl]-acetyl}-hydrazinocarbonyl)-7-oxo-1,6-diaza-bicyclo[3.2.1]oct-6-yl]ester Pre-cooled trifluoro acetic acid (100 ml, 1.307 mol) was added to tetrabutyl ammonium salt of (2S,5R)-2-(N'-{2-[2-(2-N-tert-butoxycarbonylamino-ethoxy)-phenyl]-acetyl}-hydrazinocarbonyl)-7-oxo-6-sulphooxy-1,6-diaza-bicyclo [3.2.1]octane (40 g, 50.06 mmol) while maintaining the reaction temperature between −10° C. to −5° C. The reaction mixture was stirred for 1.5 hours at −10° C. to −5° C. The mixture was evaporated below 30° C. by using vacuum. The oily mass was stirred with diethyl ether (500 ml) and filtered. The solid was taken in acetone (400 ml) and the pH of suspension was adjusted between 5.00 and 6.00 by using 10% solution sodium-2-ethyl hexanoate in acetone. The solid was filtered and washed with acetone (100 ml). The solid was dried to provide crude product in 25 g quantity, which was dissolved in water (12.5 ml) and the clear solution was stirred for 15 hour to effect precipitation. The suspension was filtered by adding iso-propanol (50 ml). Filtration and drying under vacuum provided 18 g of (2S,5R)-sulfuric acid mono-[2-(N'-{2-[2-(2-amino-ethoxy)-phenyl]-acetyl}-hydrazinocarbonyl)-7-oxo-1,6-diaza-bicyclo[3.2.1]oct-6-yl]ester as a solid in 79% yield.

Analysis:
Mass: 456.4 (M−1); For Molecular Formula $C_{17}H_{23}N_5O_8S$;
$^1$H NMR (DMSO-d6): δ 9.96 (br s, 2H), 7.77 (br s, 3H), 7.21-7.27 (m, 2H), 6.91-6.99 (m, 2H), 4.17 (t, 2H), 3.99 (s, 1H), 3.84 (d, 1H), 3.52 (s, 2H), 3.29-3.37 (m, 2H), 3.18 (d, 1H), 2.99 (d, 1H), 2.00-2.05 (m, 1H), 1.80-1.89 (m, 1H), 1.68-1.75 (m, 1H), 1.58-1.63 (m, 1H).

Example-3

(2S,5R)-Sulfuric Acid mono-[2-(N'-{2-[2-((R)-2-amino-propoxy)-phenyl]-acetyl}-hydrazino carbonyl)-7-oxo-1,6-diaza-bicyclo[3.2.1]oct-6-yl]ester

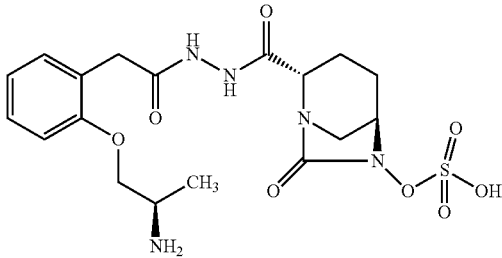 [SMILES: C[C@@H](N)COc1ccccc1CC(=O)NNC(=O)[C@@H]1CC[C@@H]2CN1C(=O)N2OS(=O)(=O)O]

Step-1: Preparation of (2S,5R)-[2-(N'-{2-[2-((R)-2-N-tert-butoxycarbonylamino-propoxy)-phenyl]-acetyl}-hydrazinocarbonyl)-7-oxo-6-benzyloxy-1,6-diaza-bicyclo[3.2.1]octane To the solution of sodium (2S,5R)-7-oxo-6-benzyloxy-1,6-diaza-bicyclo[3.2.1]octane-2-carboxylate (5.19 g, 17.41 mmol) in water (100 nil), was added EDC hydrochloride (5.2 g, 26.8 mmol) at 25° C. to 35° C. To the reaction mixture, was added 2-((R)-2-N-tert-butoxycarbonylamino-propoxy)-phenylacetic acid hydrazide (5.8 g, 17.9 mmol) dissolved in N,N-dimethylformamide (10 ml) followed by hydroxybenzotriazole (2.41 g, 17.9 mmol). The reaction mixture was stirred for 18 hours to provide a sticky solid. Solvents were decanted and the sticky solid was dissolved in ethyl acetate (200 ml). The solution was washed successively with aqueous sodium bicarbonate solution, aqueous ammonium chloride solution and aqueous brine solution. Organic layer was evaporated under vacuum to provide 8 g of (2S,5R)-[2-(N'-{2-[2-((R)-2-N-tert-butoxycarbonylamino-propoxy)-phenyl]-acetyl} hydrazine carbonyl)-7-oxo-6-benzyloxy-1,6-diaza-bicyclo[3.2.1]octane as a solid in 79% yield.

Analysis:
Mass: 582.5 (M+1), for Molecular Formula of $C_{30}H_{39}N_5O_7$;

Step-2: Preparation of (2S,5R)-[2-(N'-{2-[2-((R)-2-N-tert-butoxycarbonylamino-propoxy)-phenyl]-acetyl}-hydrazinocarbonyl)-7-oxo-6-hydroxy-1,6-diaza-bicyclo[3.2.1]octane The solution of (2S,5R)-[2-(N'-{2-[2-((R)-2-N-tert-butoxycarbonylamino-propoxy)-phenyl]-acetyl}-hydrazinocarbonyl)-7-oxo-6-benzyloxy-1,6-diaza-bicyclo[3.2.1]octane (8 g, 13.7 mmol) as obtained in step-1, in methanol (100 ml), was subjected for catalytic hydrogenolysis by using 10% palladium on carbon (2.5 g) under atmospheric hydrogen gas pressure for 2 hours at 25° C. to 35° C. The suspension was filtered through celite bed and was washed with methanol (50 ml). The filtrate was evaporated below 40° C. using vacuum. The obtained crude mass was added ethyl acetate (100 ml) and evaporated under vacuum to provide 6.2 g of (2S,5R)-[2-(N'-{2-[2-((R)-2-N-tert-butoxycarbonylamino-propoxy)-phenyl]-acetyl}-hydrazinocarbonyl)-7-oxo-6-hydroxy-1,6-diaza-bicyclo[3.2.1]octane intermediate as a solid in 91% yield, which was used immediately for the next reaction.

Analysis:
Mass: 490.5 (M−1), for Molecular formula of $C_{23}H_{33}N_5O_7$.

Step-3: Preparation of Tetrabutyl Ammonium Salt of (2S,5R)-[2-(N'-{2-[2-((R)-2-N-tert-butoxycarbonylamino-propoxy)-phenyl]-acetyl}-hydrazinocarbonyl)-7-oxo-6-sulphooxy-1,6-diaza-bicyclo[3.2.1]octane To the solution of (2S,5R)-[2-(N'-{2-[2-((R)-2-N-tert-butoxycarbonylamino-propoxy)-phenyl]-acetyl}-hydrazinocarbonyl)-7-oxo-6-hydroxy-1,6-diaza-bicyclo[3.2.1]octane (6.2 g, 12.6 mmol) as obtained in step-2, in dichloromethane (70 ml) was charged triethylamine (5.30 ml, 37.8 mmol) followed by sulfur trioxide pyridine complex (4.02 g, 25.2 mmol) at 25° C. to 35° C. The clear solution was stirred for 3 hours. To the reaction mixture was added tetrabutylammonium sulfate (4.27 g, 12.6 mmol) and it was stirred for 1 hours. To the reaction mixture was added 0.5M aqueous potassium dihydrogenothrophosphate solution (100 ml). The mixture was extracted with dichloromethane (100 ml×2). Combined organic layer was evaporated under vacuum to provide crude mass which was purified by silica gel column chromatography to yield 6 g of tetrabutyl ammonium salt of (2S,5R)-[2-(N'-{2-[2-((R)-2-N-tert-butoxycarbonylamino-propoxy)-phenyl]-acetyl}-hydrazinocarbonyl)-7-oxo-6-sulphooxy-1,6-diaza-bicyclo[3.2.1]octane intermediate as a solid in 58% yield.

Analysis:
Mass: 570.3 (M−1) as a free sulfonic acid, for Molecular Formula of $C_{23}H_{33}N_5O_{10}S \cdot N(C_4H_9)_4$.

Step-4: Preparation of (2S,5R)-sulfuric Acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester To the solution of tetrabutyl ammonium salt of (2S,5R)-[2-(N'-{2-[2-((R)-2-N-tert-butoxycarbonylamino-propoxy)-phenyl]-acetyl}-hydrazinocarbonyl)-7-oxo-6-sulphooxy-1,6-diaza-bicyclo[3.2.1]octane (6 g, 7.37 mmol) in dichloromethane (15 ml) was added trifluoro acetic acid (15 ml) while maintaining the reaction temperature between −10° C. to −5° C. The reaction mixture was stirred for 1.5 hour at −10° C. to −5° C. The mixture was evaporated below 30° C. by using vacuum. The oily mass was stirred with diethyl ether (100 ml) and filtered. The solid was suspended in dichloromethane (100 ml) and stirred for 1 hour and then filtered. The wet solid was washed with dichloromethane (100 ml). The solid was dried to provide 3.2 g of (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester as a solid m 92% yield.

Analysis:

Mass: Mass: 470.3 (M−1); For Molecular Formula $C_{18}H_{25}N_5O_8S$.

$^1$H NMR (DMSO-d6)): δ 10.02 (s, 1H), 9.98 (s, 1H), 7.84 (br s, 3H), 7.22-7.28 (m, 2H), 6.93-7.00 (m, 2H), 4.17 (dd, 1H), 4.01 (s, 1H), 3.94-3.99 (m, 1H), 3.85 (d, 1H), 3.64-3.72 (m, 1H), 3.55 (s, 2H), 3.19 (d, 1H), 3.01 (d, 1H), 1.70-1.95 (m, 1H), 1.84-1.93 (m, 1H), 1.70-1.95 (m, 1H), 1.45-1.67 (m, 1H), 1.30 (d, 3H).

Compounds 4 to 65 (Table 1) were prepared using corresponding $R_1CH_2$—$CONHNH_2$. Amine function bearing compounds of invention were prepared as per procedure described in example-2 or example-3. Other compounds were synthesized by using procedure described in example-1 either from step-1 to step-5 or by using step-1 to step-3, and 5).

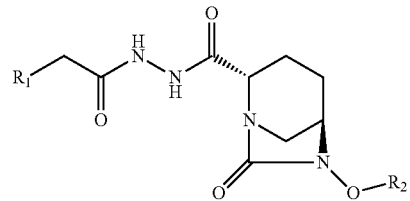

Formula (I)

TABLE 1

| Example No. | R₁CH₂—CONHNH₂ (Acid hydrazide) | R₁ | ¹H NMR | Mass (Molecular Formula) |
|---|---|---|---|---|
| 4 | benzyl-CONHNH₂ | phenyl | (DMSO-d6): δ 9.83-10.06 (br s, 2H), 7.16-7.30 (m, 5H), 3.98 (s, 1H), 3.80 (d, 1H), 3.45 (s, 2H), 3.22 (d, 1H), 2.97 (d, 1H), 1.98-2.03 (m, 1H), 1.80-1.88 (m, 1H), 1.55-1.74 (m, 2H). | 397.1 (M-1); as a free sulfonic acid ($C_{15}H_{17}N_4O_7SNa$) |
| 5 | phenethyl-CONHNH₂ | benzyl | (DMSO-d6): δ 9.88 (br s, 2H), 7.18-7.30 (m, 5H), 4.01 (s, 1H), 3.82 (d, 1H), 3.02 (d, 1H), 2.84 (t, 2H), 2.42 (t, 2H), 1.98-2.08 (m, 1H), 1.85-1.92 (m, 1H), 1.60-1.78 (m, 2H). | 411.4 (M-1); as a free sulfonic acid ($C_{16}H_{19}N_4O_7SNa$) |
| 6 | 3-phenylpropyl-CONHNH₂ | phenethyl | (DMSO-d6): δ 9.79 (s, 1H), 9.67 (s, 1H), 7.24-7.29 (m, 2H), 7.14-7.20 (m, 3H), 3.99 (s, 1H), 3.79 (s, 1H), 3.23 (d, 1H), 2.98 (d, 1H), 2.56 (t, 2H), 2.11 (t, 2H), 1.98-2.03 (m, 1H), 1.56-1.83 (m, 5H). | 425.5 (M-1); as a free sulfonic acid ($C_{17}H_{21}N_4O_7SNa$) |
| 7 | diphenylmethyl-CH₂CONHNH₂ | diphenylmethyl | (DMSO-d6): δ 9.87 (d, 2H), 7.27-7.28 (m, 10H), 4.51 (t, 1H), 3.99 (s, 1H), 3.77 (d, 1H), 3.19-3.22 (m, 2H), 2.86-2.97 (m, 2H), 1.65-1.99 (m, 4H). | 469.5 (M-1); as a free sulfonic acid ($C_{22}H_{23}N_4O_7SNa$) |
| 8 | pyridin-2-ylmethyl-CH₂CONHNH₂ | pyridin-2-yl | (DMSO-d6): δ 10.07 (s, 1H), 9.94 (s, 1H), 8.48 (d, 1H), 7.73-7.78 (m, 1H), 7.42 (d, 1H), 7.25-7.28 (m, 1H), 3.99 (s, 1H), 3.83 (d, 1H), 3.68 (s, 2H), 3.24 (d, 1H), 2.99 (br d, 1H), 1.60-2.05 (m, 4H). | 398.3 (M-1); as a free sulfonic acid ($C_{14}H_{16}N_5O_7SNa$) |
| 9 | (4-chlorophenyl)methyl-CH₂CONHNH₂ | 4-chlorophenyl | (DMSO-d6): δ 10.00 (s, 1H), 9.88 (s, 1H), 7.30-7.38 (m, 4H), 4.00 (s, 1H), 3.81 (d, 1H), 3.47 (s, 2H), 3.20-3.25 (m, 1H), 2.99 (d, 1H), 1.99-2.05 (m, 1H), 1.85-1.87 (m, 1H), 1.60-1.75 (m, 2H). | 431.2 (M-1); as free sulfonic acid ($C_{15}H_{16}N_4O_7SClNa$) |

TABLE 1-continued

| Example No. | R₁CH₂—CONHNH₂ (Acid hydrazide) | R₁ | ¹H NMR | Mass (Molecular Formula) |
|---|---|---|---|---|
| 10 | CH₂CONHNH₂ on 4-cyanophenyl | 4-cyanophenyl | (DMSO-d6): δ 10.07 (br s, 1H), 9.95 (br s, 1H), 7.79 (d, 2H), 7.50 (d, 2H), 3.99 (s, 1H), 3.82 (d, 1H), 3.60 (s, 2H), 3.20 (d, 1H), 2.98 (d, 1H), 1.97-2.04 (m, 1H), 1.81-1.87 (m, 1H), 1.65-1.75 (m, 1H), 1.57-1.64 (m, 1H). | 422.2 (M-1); as free sulfonic acid (C₁₆H₁₆N₅O₇SNa) |
| 11 | CH₂CONHNH₂ on 4-(boc-NH)phenyl | 4-aminophenyl (H₂N) | (DMSO-d6): δ 9.99 (s, 1H), 9.87 (s, 1H), 9.25 (br s, 3H), 7.36 (d, 2H), 7.21 (d, 2H), 3.98 (s, 1H), 3.80 (d, 1H), 3.48 (s, 2H), 3.16-3.20 (m, 1H), 2.97 (d, 1H), 1.97-2.02 (m, 1H), 1.80-1.87 (m, 1H), 1.67-1.73 (m, 1H), 1.54-1.58 (m, 1H). | 412.2 (M-1) (C₁₅H₁₉N₅O₇S) |
| 12 | CH₂CONHNH₂ on 4-(boc-NHCH₂)phenyl | 4-(aminomethyl)phenyl (H₂N-CH₂-) | (DMSO-d6): δ 10.02 (s, 1H), 9.90 (s, 1H), 8.07 (br s, 3H), 7.34-7.40 (m, 4H), 4.00-4.03 (m, 3H), 3.82 (d, 1H), 3.49 (s, 2H), 3.21 (d, 1H), 2.98 (d, 1H), 1.98-2.04 (m, 1H), 1.81-1.86 (m, 1H), 1.62-1.76 (m, 1H), 1.55-1.60 (m, 1H). | 426.2 (M-1) (C₁₆H₂₁N₅O₇S) |
| 13 | CH₂CONHNH₂ on 4-(dimethylamino)phenyl | 4-(dimethylamino)phenyl | (DMSO-d6): δ 9.90 (s, 1H), 9.84 (s, 1H), 7.11 (d, 2H), 6.68 (d, 2H), 3.99 (s, 1H), 3.80 (d, 1H), 3.23-3.37 (m, 3H), 2.98 (d, 1H), 2.85 (s, 6H), 1.97-2.04 (m, 1H), 1.83-1.90 (m, 1H), 1.61-1.71 (m, 2H). | 440.4 (M-1); as free sulfonic acid (C₁₇H₂₂N₅O₇SNa) |
| 14 | CH₂CONHNH₂ on 4-methoxyphenyl | 4-methoxyphenyl | (DMSO-d6): δ 9.92 (s, 1H), 9.85 (s, 1H), 7.19 (d, 2H), 6.84 (d, 2H), 3.97 (s, 1H), 3.79 (d, 1H), 3.70 (s, 3H), 3.36 (s, 2H), 3.22 (d, 1H), 2.95 (d, 1H), 1.97-2.02 (m, 1H), 1.82-1.85 (m, 1H), 1.57-1.70 (m, 2H). | 427.3 (M-1); as free sulfonic acid (C₁₆H₁₉N₄O₈SNa) |
| 15 | CH₂CONHNH₂ on 2-ethoxyphenyl | 2-ethoxyphenyl | (DMSO-d6): δ 9.84 (s, 2H), 7.25 (d, 1H), 7.17-7.21 (m, 1H), 6.93 (d, 1H), 6.85-6.89 (m, 1H), 3.98-4.04 (m, 3H), 3.82 (d, 1H), 3.44 (s, 2H), 3.24 (d, 1H), 2.98 (d, 1H), 1.99-2.05 (m, 1H), 1.82-1.87 (m, 1H), 1.60-1.75 (m, 2H), 1.34 (t, 3H). | 441.2 (M-1); as free sulfonic acid (C₁₇H₂₁N₄O₈SNa) |

TABLE 1-continued

| Example No. | R₁CH₂—CONHNH₂ (Acid hydrazide) | R₁ | ¹H NMR | Mass (Molecular Formula) |
|---|---|---|---|---|
| 16 | CH₂CONHNH₂ attached to 2-fluoro-4-(boc-NH)-phenyl with OEt (ethoxy) — structure shows 3-fluoro-4-ethoxyphenyl with boc-NH | 3-fluoro-4-ethoxyphenyl (with F and OEt) | (DMSO-d6): 9.96 (br s, 1H), 9.88 (br s, 1H), 7.26 (t, 1H), 6.71–6.78 (m, 2H), 3.99–4.04 (m, 3H), 3.81 (d, 1H), 3.43 (s, 2H), 3.22 (d, 1H), 2.97 (d, 1H), 1.99–2.12 (m, 1H), 1.82–1.85 (m, 1H), 1.59–1.76 (m, 2H), 1.31 (t, 3H). | 459.2 (M-1); as free sulfonic acid (C₁₇H₂₀N₄O₈FSNa) |
| 17 | CH₂CONHNH₂ attached to 3-fluoro-4-(boc-NH)phenyl | 4-amino-3-fluorophenyl (H₂N, F) | (DMSO-d6): δ 9.98 (s, 1H), 9.91 (s, 1H), 7.25 (t, 1H), 6.75 (d, 2H), 4.10 (br s, 2H), 3.99 (s, 1H), 3.81 (d, 1H), 3.44 9s, 2H), 3.21 (d, 1H), 2.98 (d, 1H), 1.97–2.04 (m, 1H), 1.80–1.86(m, 1H), 1.65–1.74(m, 1H), 1.55–1.63 (m, 1H). | 430.3 (M-1) (C₁₅H₁₈N₅O₇FS) |
| 18 | CH₂CONHNH₂ attached to 3-fluoro-4-(TBDMS-O)phenyl | 3-fluoro-4-hydroxyphenyl (F, HO) | (DMSO-d6): δ 9.93 (br s, 2H), 7.12 (t, 1H), 6.46–6.53 (m, 2H), 3.97 (s, 1H), 3.74 (d, 1H), 3.39 (s, 1H), 3.35 (s, 2H), 3.27 (d, 1H), 2.94 (d, 1H), 1.99–2.05 (m, 1H), 1.81–1.85 (m, 1H), 1.61–1.71 (m, 2H). | 431.2 (M-1); as free sulfonic acid (C₁₅H₁₆N₄O₈FSNa) |
| 19 | CH₂CONHNH₂ attached to 2-hydroxyphenyl | 4-(alanyl ester)phenyl (H₂N-CH(CH₃)-C(=O)-O-) | (DMSO-d6): δ 9.85 (br s, 31-1); 7.16–7.18 (m, 1H), 7.02–7.06 (m, 1H), 6.81 (d, 1H), 6.70–6.74 (m, 1H), 3.99 (s, 1H), 3.81 (d, 1H), 3.42 (s, 2H), 3.24 (d, 1H), 3.98 (d, 1H), 1.85–2.04 (m, 1H), 1.82–1.86 (m, 1H), 1.60–1.76 (m, 2H). | 413.2 (M-1) (C₁₅H₁₇N₄O₈SNa) |
| 20 | CH₂CONHNH₂ attached to 3-(TBDMS-O)phenyl | 3-hydroxyphenyl (OH) | (DMSO-d6): δ 9.55 (br s, 1H), 9.31 (s, 2H), 7.07 (t, 1H), 6.60–6.71 (m, 3H), 3.99 (s, 1H), 3.80 (d, 1H), 3.35 (s, 2H), 3.24 (d, 1H), 2.97 (d, 1H), 1.99–2.04 (m, 1H), 1.82–1.87 (m, 1H), 1.60–1.74 (m, 2H). | 413.4 (M-1); as free sulfonic acid (C₁₅H₁₇N₄O₈SNa) |
| 21 | CH₂CONHNH₂ attached to 2-(boc-NH)phenyl | 2-aminophenyl (NH₂) | (DMSO-d6): δ δ 9.99 (s, 1H), 9.87 (s, 1H), 9.25 (br s, 3H), 7.16–7.18 (m, 1H), 7.02–7.06 (m, 1H), 6.81 (d, 1H), 6.70–6.74 (m, 1H), 3.99 (s, 1H), 3.81 (d, 1H), 3.42 (s, 2H), 3.24 (d, 1H), 3.98 (d, 1H), 1.85–2.04 (m, 1H), 1.82–1.86 (m, 1H), 1.60–1.76 (m, 2H). | 412.2 (M-1) (C₁₅H₁₉N₅O₇S) |

TABLE 1-continued

| Example No. | R₁CH₂—CONHNH₂ (Acid hydrazide) | R₁ | ¹H NMR | Mass (Molecular Formula) |
|---|---|---|---|---|
| 22 | 4-(pivaloyloxy)phenyl-CH₂CONHNH₂ | 4-(pivaloyloxy)phenyl | (DMSO-d6) = 10.04 (s, 1H), 9.92 (s, 1H), 7.33 (d, 2H), 7.02 (d, 2H), 3.99 (s, 1H), 3.82 (d, 1H), 3.48 (s, 2H), 3.23 (d, 1H), 2.99 (d, 1H), 2.00-2.05 (m, 1H), 1.82-1.85 (m, 1H), 1.68-1.74 (m, 1H), 1.60-1.64 (m, 1H), 1.29 (s, 9H). | 497.4.4 (M-1); as a free sulfonic acid (C₂₀H₂₅N₄O₉SNa) |
| 23 | 4-(N-boc-L-alanyloxy)phenyl-CH₂CONHNH₂ | 4-(L-alanyloxy)phenyl | (DMSO-d6): δ 10.03 (s, 1H), 9.90 (s, 1H), 8.40 (br s, 3H), 7.37 (d, 2H), 7.11 (d, 2H), 4.40 (q, 1H), 3.97 (s, 1H), 3.65 (d, 1H), 3.49 (s, 2H), 3.20 (d, 1H), 2.97 (d, 1H), 1.83-2.03 (m, 1H), 1.73-1.82 (m, 1H), 1.66-1.70 (m, 2H), 1.58 (d, 3H). | 484.4 (M-1) (C₁₈H₂₃N₅O₉S) |
| 24 | 4-(N-boc-L-valyloxy)phenyl-CH₂CONHNH₂ | 4-(L-valyloxy)phenyl | (DMSO-d6): δ 10.03 (s, 1H), 9.90 (s, 1H), 8.43 (br s, 3H), 7.38 (d, 2H), 7.11 (d, 2H), 4.23 (s, 1H), 3.97 (s, 1H), 3.80 (d, 1H), 3.49 (s, 2H), 3.10 (d, 1H), 2.97 (d, 1H), 2.65-2.95 (m, 1H), 2.29-2.33 (m, 1H), 1.83-2.02 (m, 1H), 1.54-1.70 (m, 2H), 1.05-1.10 (m, 6H). | 512.5 (M-1) (C₂₀H₂₇N₅O₉S) |
| 25 | 4-(N-boc-L-prolyloxy)phenyl-CH₂CONHNH₂ | 4-(L-prolyloxy)phenyl | (DMSO-d6) = 10.06 (s, 1H), 9.93 (s, 1H), 9.23 (br s, 2H), 7.07 (d, 2H), 6.67 (d, 2H), 4.68 (t, 1H), 3.99 (s, 1H), 3.82 (d, 1H), 3.54 (s, 2H), 3.16-3.25 (m, 3H), 2.98 (d, 1H), 2.40-2.50 (m, 1H), 2.19-2.26 (m, 1H), 1.92-2.00 (m, 3H), 1.83-1.87 (m, 1H), 1.56-1.72 (m, 2H). | 510.4 (M-1) (C₂₀H₂₅N₅O₉S) |
| 26 | 4-(3-tert-butoxy-3-oxopropanoyloxy)phenyl-CH₂CONHNH₂ | 4-(3-tert-butoxy-3-oxopropanoyloxy)phenyl | (DMSO-d6) = 10.03 (s, 1H), 9.92 (s, 1H), 7.31-7.36 (m, 2H), 7.05 (d, 2H), 3.99 (s, 2H), 3.81 (d, 1H), 3.48 (d, 2), 3.16-3.24 (m, 2H), 2.98 (d, 1H), 2.00-2.04 (m, 1H), 1.85-1.89 (m, 1H), 1.69-1.72 (m, 1H), 1.61-1.64 (m, 1H), 1.43 (d, 9H). | 555.3 (M-1); as a free sulfonic acid (C₂₂H₂₇N₄O₁₁SNa) |

TABLE 1-continued

| Example No. | R₁CH₂—CONHNH₂ (Acid hydrazide) | R₁ | ¹H NMR | Mass (Molecular Formula) |
|---|---|---|---|---|
| 27 | CH₂CONHNH₂ attached to para-substituted phenyl with O-C(=O)-CH₂CH₂-C(=O)-O-tBu | para-substituted phenyl with O-C(=O)-CH₂CH₂-C(=O)-O-tBu | (DMSO-d6) = 9.85 (br s, 2H), 7.30 (d, 2H), 6.99 (d, 2H), 3.97 (s, 1H), 3.80 (d, 1H), 3.45 (s, 2H), 3.20 (d, 1H), 2.97 (d, 1H), 2.72-2.75 (m, 1H), 2.52-2.55 (m, 1H), 2.47 (s, 1H), 2.32-2.39 (m, 1H), 1.98-2.02 (m, 1H), 1.80-1.82 (m,1H), 1.58-1.69 (m, 2H), 1.37 (s, 9H). | 565.5 (M-1); as a free sulfonic acid (C₂₃H₂₉N₄O₁₁SNa) |
| 28 | CH₂CONHNH₂ attached to para-substituted phenyl with O-C(=O)-NH-cyclohexyl | para-substituted phenyl with O-C(=O)-NH-cyclohexyl | (DMSO-d6): δ 10.03 (s, 1H), 7.68 (d, 1H), 7.27 (d, 2H), 7.02 (d, 2H), 3.98 (s, 1H), 3.81 (d, 1H), 3.45 (s, 2H), 3.30 (s, 1H), 3.23 (d, 1H), 2.98 (br d, 1H), 2.00-2.03 (m, 1H), 1.54-1.83 (m, 8H), 1.11-1.28 (m, 5H). | 538.4 (M-1); as free sulfonic acid (C₂₂H₂₈N₅O₉SNa) |
| 29 | CH₂CONHNH₂ attached to para-substituted phenyl with O-C(=O)-NH-CH(iPr)-C(=O)-O-tBu (valine-tBu carbamate) | para-substituted phenyl with O-C(=O)-NH-CH(iPr)-C(=O)-O-tBu | (DMSO-d6): 9.99 (br s, 2H), 8.02 (d, 1H), 7.29 (d, 2H), 7.02 (d, 2H), 3.98 (s, 1H), 3.80-3.85 (m, 2H), 3.46 (s, 2H), 3.23 (d, 1H), 2.98 (d, 1H), 1.61-2.07 (m, 5H), 1.42 (s, 9H), 0.94 (d, 6H). | 612.5 (M-1); as free sulfonic acid (C₂₅H₃₄N₅O₁₁SNa) |
| 30 | CH₂CONHNH₂ attached to para-substituted phenyl with O-CH₂CH₂-NH-boc | para-substituted phenyl with O-CH₂CH₂-NH₂ | (DMSO-d6): δ 9.99 (s, 1H), 9.80 (s, 1H), 7.88 (br s, 3H), 7.18-7.24 (m, 2H), 6.86-6.92 (m, 2H), 4.10-4.17 (m, 2H), 3.97 (s, 2H), 3.80 (d, 1H), 3.37 (s, 2H), 3.18-3.21 (m, 3H), 2.96 (d, 1H), 1.96-2.00 (m, 1H), 1.83-1.95 (m, 1H), 1.56-1.72 (m, 2H). | 4564 (M-1) (C₁₇H₂₃N₅O₈S) |

TABLE 1-continued

| Example No. | R₁CH₂—CONHNH₂ (Acid hydrazide) | R₁ | ¹H NMR | Mass (Molecular Formula) |
|---|---|---|---|---|
| 31 | [structure: CH₂CONHNH₂ with fluoro-phenoxy-ethyl-NHboc] | [structure: fluoro-phenoxy-ethyl-NH₂] | (DMSO-d6): δ 9.99 (s, 1H), 9.90 (s, 1H), 7.92 (br s, 3H), 7.33 (t, 1H), 6.78-6.87 (m, 2H), 4.16 (t, 2H), 3.99 (s, 1H), 3.82 (d, 1H), 3.46 (s, 2H), 3.19-3.23 (m, 3H), 2.98 (d, 1H), 1.97-2.04 (m, 1H), 1.81-1.87 (m, 1H), 1.68-1.75 (m, 1H), 1.54-1.64 (m, 1H). | 474.2 (M-1) ($C_{17}H_{22}N_5O_8FS$) |
| 32 | [structure: CH₂CONHNH₂ with phenoxy-ethyl-NHboc] | [structure: phenoxy-ethyl-NH₂] | (DMSO-d6): δ 10.01 (s, 1H), 9.90 (s, 1H), 7.92 (br s, 3H), 7.23-7.27 (m, 1H), 6.85-6.96 (m, 3H), 4.14 (s, 2H), 4.00 (s, 1H), 3.82 (d, 1H), 3.46 (s, 2H), 3.10-3.40 (m, 3H), 2.98 (d, 1H), 1.99-2.07 (m, 1H), 1.83-1.89 (m, 1H), 1.58-1.72 (m, 2H). | 456.4 (M-1) ($C_{17}H_{23}N_5O_8S$) |
| 33 | [structure: CH₂CONHNH₂ with phenoxy-ethyl-OTBS] | [structure: phenoxy-ethyl-OH] | (DMSO-d6): δ 9.85 (s, 1H), 7.12 (d, 1H), 7.00-7.04 (m, 1H), 6.68-6.75 (m, 2H), 3.98 (br s, 2H), 3.79 (d, 1H), 3.74 (t, 1H), 3.46 (d, 1H), 3.40 (s, 2H), 3.24 (d, 1H), 3.14 (d, 1H), 2.98 (d, 1H), 2.01-2.08 (m, 1H), 1.82-1.90 (m, 1H), 1.55-1.75 (m, 2H). | 457.3 (M-1); for free sulfonic acid ($C_{17}H_{21}N_4O_9SNa$) |
| 34 | [structure: CH₂CONHNH₂ with phenoxy-propyl-NHboc] | [structure: phenoxy-propyl-NH₂] | (DMSO-d6): δ 9.88 (br s, 2H), 7.65 (br s, 3H), 7.21-7.27 (m, 2H), 6.88-6.96 (m, 2H), 4.05-4.08 (m, 1H), 4.00 (s, 2H), 3.84 (d, 1H), 3.47 (s, 2H), 3.21 (d, 1H), 3.02-3.05 (m, 3H), 2.00-2.07 (m, 3H), 1.83-1.87 (m, 1H), 1.69-1.73 (m, 1H), 1.59-1.62 (m, 2H). | 470.4 (M-1) ($C_{18}H_{25}N_5O_8S$) |
| 35 | [structure: CH₂CONHNH₂ with phenoxy-propyl-NHboc] | [structure: phenoxy-propyl-NH₂] | (DMSO-d6): δ 9.99 (s, 1H), 9.90 (s, 1H), 7.68 (br s, 3H), 7.22 (t, 1H), 6.92 (s, 1H), 6.85 (d, 1H), 6.81 (dd, 1H), 4.03-4.06 (m, 2H), 4.00 (s, 1H), 3.83 (d, 1H), 3.44 (d, 2H), 3.22 (d, 1H), 2.94-2.99 (m, 3H), 2.03 (m, 3H), 1.82-1.91 (m, 1H), 1.35-1.80 (m, 2H). | 470.3 (M-1) ($C_{18}H_{25}N_5O_8S$) |

TABLE 1-continued
| Example No. | R₁CH₂—CONHNH₂ (Acid hydrazide) | R₁ | ¹H NMR | Mass (Molecular Formula) |
|---|---|---|---|---|
| 36 |  |  | (DMSO-d6): δ 10.00 (s, 1H), 9.97 (s, 1H), 8.35 (br , 2H), 7.24-7.29 (m, 2H), 6.93-7.02 (m, 2H), 4.24 (t, 2H), 4.01 (s, 1H), 3.86 (d, 1H), 3.53 (s, 2H), 3.37-3.41 (m, 2H), 3.19 (d, 1H), 3.00 (d, 1H), 2.69 (t, 3H), 2.01-2.08 (m, 1H), 1.83-1.88 (m, 1H), 1.68-1.77 (m, 1H), 1.57-1.62 (m, 1H). | 470.3 (M-1) (C₁₈H₂₅N₅O₈S) |
| 37 |  |  | (DMSO-d6): δ 10.01 (s, 1H), 9.91 (s, 1H), 8.55 (br s, 2H), 7.25 (t, 2H), 6.85-6.93 (m, 2H), 4.20 (t, 2H), 4.00 (s, 1H), 3.83 (d, 1H), 3.46 (s, 2H), 3.31-3.41 (m, 2H), 3.22 (d, 1H), 2.99 (d, 1H), 2.66 (s, 3H), 1.98-2.04 (m, 1H), 1.82-1.8 7m, 1H), 1.69-1.77 (m, 1H), 1.56-1.65 (m, 1H). | 470.3 (M-1) (C₁₈H₂₅N₅O₈S) |
| 38 |  |  | (DMSO-d6): δ 9.96 (s, 1H), 9.88 (s, 1H), 8.54 (br s, 2H), 7.25 (d, 2H), 6.94 (d, 2H), 3.41 (s, 2H), 3.30-3.39 (m, 2H), 3.22 (d, 1H), 2.98 (d, 1H), 2.63-2.66 (m, 3H), 1.98-2.07 (m, 1H), 1.84-1.88 (m, 1H), 1.68-1.73 (m, 1H), 1.58-1.61 (m, 1H). | 470.3 (M-1) (C₁₈H₂₅N₅O₈S) |
| 39 |  |  | (DMSO-d6): δ 9.97 (s, 1H), 9.88 (s, 1H), 8.53 (br s, 2H), 7.31 (t, 1H), 6.78-6.86 (m, 2H), 4.20 (t, 2H), 3.98 (s, 1H), 3.80 (d, 1H), 3.44 (s, 2H), 3.30 (t, 2H), 3.20 (d, 1H), 2.96 (d, 1H), 2.62 (s, 3H), 1.97-2.02 (m, 1H), 1.80-1.86 (m, 1H), 1.66-1.73 (m, 1H), 1.55-1.62 (m, 1H). | 488.4 (M-1) (C₁₈H₂₄N₅O₈FS) |

TABLE 1-continued

| Example No. | $R_1CH_2$—CONHNH$_2$ (Acid hydrazide) | $R_1$ | $^1$H NMR | Mass (Molecular Formula) |
|---|---|---|---|---|
| 40 | CH$_2$CONHNH$_2$, 2-(BocNH-CH(CH$_3$)-CH$_2$-O-)phenyl | 2-(H$_2$N-CH(CH$_3$)-CH$_2$-O-)phenyl | (DMSO-d6): δ 9.99 (br s, 2H), 7.85 (br s, 3H), 7.23-7.29 (m, 2H), 6.93-7.00 (m, 2H), 4.13-4.17 (dd, 1H), 4.01 (s, 1H), 3.94-3.99 (m, 1H), 3.85 (d, 1H), 3.68-3.69 (m, 1H), 3.55 (s, 2H), 3.21 (d, 1H), 2.99-3.02 (m, 1H), 2.01-2.06 (m, 1H), 1.83-1.92 (m, 1H), 1.70-1.76 (m, 1H), 1.56-1.64 (m, 1H), 1.29 (d, 3H). | 470.5 (M-1) (C$_{18}$H$_{25}$N$_5$O$_8$S) |
| 41 | CH$_2$CONHNH$_2$, 3-(BocNH-CH(CH$_3$)-CH$_2$-O-)phenyl | 3-(H$_2$N-CH(CH$_3$)-CH$_2$-O-)phenyl | (D2O): δ 7.24 (t, 1H), 6.83-6.91 (m, 3H), 4.14-4.17 (m, 1H), 4.07-4.09 (m, 1H), 4.04 (d, 1H), 3.93-3.97 (m, 1H), 3.67-3.71 (m, 1H), 3.58 (s, 2H), 3.22 (d, 1H), 3.08 (d, 1H), 2.06-2.14 (m, 1H), 1.90-1.99 (m, 1H), 1.78-1.89 (m, 1H), 1.65-1.73 (m, 1H), 1.29 (d, 3H). | 470.4 (M-1) (C$_{18}$H$_{25}$N$_5$O$_8$S) |
| 42 | CH$_2$CONHNH$_2$, 3-(BocNH-CH(CH$_3$)-CH$_2$-O-)phenyl | 3-(H$_2$N-CH(CH$_3$)-CH$_2$-O-)phenyl | (DMSO-d6): δ 10.01 (s, 1H), 9.91 (s, 1H), 7.95 (br s, 3H), 7.25 (t, 1H), 6.99 (s, 1H), 6.85-6.95 (m, 2H), 4.09-4.13 (m, 1H), 4.00 (s, 1H), 3.92-3.96 (m, 1H), 3.81 (d, 1H), 3.62 (br s, 1H), 3.46 (s, 2H), 3.22 (d, 1H), 2.99 (d, 1H), 2.01-2.05 (m, 1H), 1.81-1.88 (m, 1H), 1.67-1.75 (m, 1H), 1.56-1.64 (m, 1H), 1.27 (d, 3H). | 470.3 (M-1) (C$_{18}$H$_{25}$N$_5$O$_8$S) |

TABLE 1-continued

| Example No. | R₁CH₂—CONHNH₂ (Acid hydrazide) | R₁ | ¹H NMR | Mass (Molecular Formula) |
|---|---|---|---|---|
| 43 | | | (DMSO-d6): δ 9.96 (s, 1H), 9.88 (s, 1H), 7.93 (br s, 3H),7.24 (d, 2H), 6.94 (d, 2H), 4.08-4.12 (m, 1H), 4.00 (s, 1H), 3.90-3.94 (m, 1H), 3.82 (d, 1H), 3.61 (br s, 1H), 3.41 (s, 2H), 3.22 (d, 1H), 2.98 (d, 1H), 1.98-2.08 (m, 1H), 1.83-1.86 (m, 1H), 1.68-1.75 (m, 1H), 1.58-1.63 (m, 1H), 1.26 (d, 3H). | 470.3 (M-1) (C₁₈H₂₅N₅O₈S) |
| 44 | | | (DMSO-d6): δ 9.99 (s, 1H), 9.90 (s, 1H), 7.92 (br s, 3H), 7.33 (t, 1H), 6.80-6.87 (m, 2H), 4.11-4.16 (m, 1H), 3.93-4.00 (m, 2H), 3.82 (d, 1H), 3.57-3.62 (m, 1H), 3.45 (s, 2H), 3.22 (d, 1H), 2.98 (d, 1H), 1.97-2.05 (m, 1H), 1.83-1.87 (m, 1H), 1.65-1.75 (m, 1H), 1.54-1.64 (m, 1H), 1.25 (d, 3H). | 488.3 (M-1) (C₁₈H₂₄N₅O₈FS) |
| 45 | | | (DMSO-d6): δ 9.99 (s, 1H), 9.89 (s, 1H), 7.94 (br s, 3H), 7.32 (t, 1H), 6.80-6.86 (m, 2H), 4.13 (dd, 1H), 3.93-3.97 (m, 2H), 3.82 (d, 1H), 3.62 (br s, 1H), 3.45 (s, 2H), 3.21 (d, 1H), 2.97 (d, 1H), 1.99-2.07 (m, 1H), 1.83-1.86 (m, 1H), 1.68-1.72(m, 1H), 1.58-1.63 (m, 1H), 1.25 (d, 3H). | 488.2 (M-1) (C₁₈H₂₄N₅O₈FS) |
| 46 | | | (DMSO-d6): δ 9.99 (s, 1H), 9.89 (s, 1H), 7.97 (br s, 3H), 7.33 (t, 1H), 6.82-6.91 (m, 2 H), 4.19 (dd, 1H), 3.99-4.06 (m, 2H), 3.82 (d, 1H), 3.46 (s, 2H), 3.33 (br s, 1H), 3.22 (d, 1H), 2.98 (d, 1H), 199-2.07 (m, 2H), 1.83-1.86 (m, 1H), 1.68-1.74 (m, 1H), 1.58-1.63 (m, 1H), 0.97-1.03 (m, 6H). | 516.3 (M-1) (C₂₀H₂₈N₅O₈FS) |

TABLE 1-continued

| Example No. | R₁CH₂—CONHNH₂ (Acid hydrazide) | R₁ | ¹H NMR | Mass (Molecular Formula) |
|---|---|---|---|---|
| 47 | 4-(N-boc-pyrrolidin-3-yloxy)-2-fluorophenyl-CH₂CONHNH₂ | 4-((pyrrolidin-3-yl)oxy)-2-fluorophenyl | (DMSO-d6): δ 9.99 (s, 1H), 9.90 (s, 1H), 9.02 (br s, 1H), 8.84 (br s, 1H), 7.35 (t, 1H), 6.88 (dd, 1H), 6.79 (dd, 1H), 5.14 (s, 1H), 3.99 (s, 1H), 3.70-3.87 (m, 3H), 3.45 (s, 2H), 3.29-3.46 (m, 2H), 3.22 (d, 2H), 2.98 (d, 1H), 2.18-2.26 (m, 1H), 1.99-2.14 (m, 1H), 1.81-1.87 (m, 1H), 1.68-1.75 (m, 1H), 1.58-1.63 (m, 1H). | 500.2 (M−1) (C₁₉H₂₄N₅O₈FS) |
| 48 | 4-((N-boc-pyrrolidin-2-yl)methoxy)-2-fluorophenyl-CH₂CONHNH₂ | 4-((pyrrolidin-2-yl)methoxy)-2-fluorophenyl | (DMSO-d6): δ 9.99 (s, 1H), 9.90 (s, 1H), 9.09 (br s, 1H), 8.67 (br s, 1H), 7.33 (t, 1H), 6.79-6.88 (m, 2H), 4.25-4.29 (m, 1H), 4.08 (t, 1H), 4.00 (s, 1H), 3.90 (br s, 1H), 3.82 (d, 1H), 3.46 (s, 2H), 3.20 (d, 1H), 3.10-3.19 (m, 2H), 2.98 (d, 1H), 2.07-2.15 (m, 1H), 1.92-2.02 (m, 2H), 1.83-1.91 (m, 2H), 1.67-1.76 (m, 2H), 1.57-1.63 (m, 1H). | 514.3 (M−1) (C₂₀H₂₆N₅O₈FS) |
| 49 | 4-((2-(N-boc-amino)propyl)oxy)phenyl-CH₂CONHNH₂ | 4-((2-aminopropyl)oxy)phenyl | (DMSO-d6): δ 9.96 (s, 1H), 9.88 (s, 1H), 7.93 (br s, 3H), 7.24 (d, 2H), 6.94 (d, 2H), 4.10 (dd, 1H), 4.08 (br s, 1H), 3.90-4.0 (m, 1H), 3.82 (d, 1H), 3.61 (br s, 1H), 3.41 (s, 2H), 3.22 (d, 1H), 2.98 (d, 1H), 1.99-2.04 (m, 1H), 1.85-1.90 (m, 1H), 1.68-1.75 (m, 1H), 1.56-1.83 (m, 1H), 1.26 (d, 3H). | 470.5 (M−1) (C₁₈H₂₅N₅O₈S) |
| 50 | 2-((2-(N-boc-amino)-3-methylbutyl)oxy)phenyl-CH₂CONHNH₂ | 2-((2-amino-3-methylbutyl)oxy)phenyl | (DMSO-d6): δ 10.06 (s, 1H), 9.99 (s, 1H), 7.90 (br s, 3H), 7.05-7.29 (m, 2H), 7.04 (d, 1H), 6.95 (t, 1H), 4.20-4.23 (m, 1H), 4.08 (t, 1H), 4.02 (s, 1H), 3.85 (d, 1H), 3.54 (s, 2H), 3.41 (br s, 1H), 3.21 (d, 1H), 3.01 (d, 1H), 2.00-2.10 (m, 2H), 1.83-1.89 (m, 1H), 1.69-1.77 (m, 1H), 1.59-1.66 (m, 1H), 1.00-1.05 (m, 6H). | 498.3 (M−1) (C₂₀H₂₉N₅O₈S) |

TABLE 1-continued

| Example No. | R₁CH₂—CONHNH₂ (Acid hydrazide) | R₁ | ¹H NMR | Mass (Molecular Formula) |
|---|---|---|---|---|
| 51 | *structure: 2-substituted phenoxy with N-boc aminobutyl, CH₂CONHNH₂* | *structure: 2-substituted phenoxy with NH₂ aminobutyl* | (DMSO-d6): δ 10.03 (s, 1H), 9.99 (s, 1H), 7.89 (br s, 3H), 7.24-7.29 (m, 2H), 7.04 (d, 1H), 6.95 (t, 1H), 4.22 (dd, 1H), 4.06-4.11 (m, 1H), 4.02 (s, 1H), 3.86 (d, 1H), 3.54 (d, 2H), 3.35-3.39 (m, 1H), 3.21 (d, 1H), 3.02 (d, 1H), 2.01-2.11 (m, 2H), 1.82-1.87 (m, 1H), 1.69-1.78 (m, 1H), 1.56-1.65 (m, 1H), 1.00-1.05 (m, 6H). | 498.3 (M-1) (C₂₀H₂₉N₅O₈S) |
| 52 | *structure: 3-substituted phenoxy with N-boc aminobutyl, CH₂CONHNH₂* | *structure: 3-substituted phenoxy with NH₂ aminobutyl* | (DMSO-d6): δ 10.01 (s, 1H), 9.92 (s, 1H), 8.00 (br s, 3H), 7.26 (t, 1H), 7.02 (s, 1H), 6.88-6.93 (m, 2H), 4.18 (dd, 1H), 4.04 (dd, 1H), 4.00 (s, 1H), 3.83 (d, 1H), 3.46 (s, 2H), 3.22 (d, 1H), 2.98 (d, 1H), 1.99-2.06 (m, 2H), 1.81-8.17 (m, 1H), 1.68-2.07 (m, 2H), 1.54-1.65 (m, 1H), 0.98-1.04 (m, 6H). | 498.4 (M-1) (C₂₀H₂₉N₅O₈S) |
| 53 | *structure: 3-substituted phenoxy with N-boc aminobutyl, CH₂CONHNH₂* | *structure: 3-substituted phenoxy with NH₂ aminobutyl* | (DMSO-d6): δ 10.01 (s, 1H), 9.92 (s, 1H), 7.00 (br s, 3H), 7.26 (t, 1H), 7.02 (s, 1H), 6.88-6.93 (m, 2H), 4.16-4.19 (m, 1H), 4.02-4.07 (m, 1H), 4.00 (s, 1H), 3.83 (d, 1H), 3.46 (s, 2H), 3.36-3.39 (m, 1H), 3.22 (d, 1H), 2.99 (d, 1H), 1.97-2.07 (m, 2H), 1.83-1.87 (m, 1H), 1.67-1.76 (m, 1H), 1.57-1.64 (m, 1H), 0.98-1.04 (m, 6H). | 498.4 (M-1) (C₂₀H₂₉N₅O₈S) |

TABLE 1-continued

| Example No. | $R_1CH_2$—CONHNH$_2$ (Acid hydrazide) | $R_1$ | $^1$H NMR | Mass (Molecular Formula) |
|---|---|---|---|---|
| 54 | [structure: 4-substituted phenoxy-CH$_2$-CH(NHboc)-CH(CH$_3$)$_2$ with CH$_2$CONHNH$_2$] | [structure: 4-substituted phenoxy-CH$_2$-CH(NH$_2$)-CH(CH$_3$)$_2$] | (DMSO-d6): δ 9.96 (s, 1H), 9.88 (s, 1H), 7.97 (br s, 3H), 7.25 (d, 2H), 6.96 (d, 2H), 4.15-4.18 (m, 1H), 3.99 (s, 2H), 3.81 (d, 1H), 3.41 (s, 2H), 3.22 (d, 1H), 2.98 (d, 1H), 1.97-2.04 (m, 2H), 1.81-1.87 (m, 1H), 1.67-1.75 (m, 1H), 1.54-1.66 (m, 1H), 1.01-1.32 (m, 1H), 0.94-0.98 (m, 6H). | 498.4 (M-1) (C$_{20}$H$_{29}$N$_5$O$_8$S) |
| 55 | [structure: 4-substituted phenoxy-CH$_2$-CH(NHboc)-CH(CH$_3$)$_2$ with CH$_2$CONHNH$_2$] | [structure: 4-substituted phenoxy-CH$_2$-CH(NH$_2$)-CH(CH$_3$)$_2$] | (DMSO-d6): δ 9.96 (s, 1H), 9.88 (s, 1H), 7.97 (br s, 3H), 7.25 (d, 2H), 6.96 (d, 2H), 4.14-4.18 (m, 1H), 4.00-4.02 (m, 2H), 3.82 (d, 1H), 3.41 (s, 2H), 3.22 (d, 1H), 2.98 (d, 1H), 1.98-2.07 (m, 2H), 1.83-1.85 (m, 1H), 1.68-1.72 (m, 2H), 1.60-1.63 (m, 1H), 0.98-1.10 (m, 6H). | 498.3 (M-1) (C$_{20}$H$_{29}$N$_5$O$_8$S) |
| 56 | [structure: 2-substituted phenoxy-CH$_2$-pyrrolidine-Nboc with CH$_2$CONHNH$_2$] | [structure: 2-substituted phenoxy-CH$_2$-pyrrolidine-NH] | (DMSO-d6) = 9.99 (s, 1H), 8.86 (br s, 1H), 8.49 (br s, 1H), 7.23-7.29 (m, 2H), 6.93-6.99 (m, 2H), 4.27-4.29 (m, 1H), 4.06-4.11 (m, 1H), 3.97-4.01 (m, 2H), 3.86 (d, 1H), 3.52 (s, 2H), 3.19-3.28 (m, 3H), 3.01 (d, 1H), 1.59-2.14 (m, 8H). | 496.4 (M-1) (C$_{20}$H$_{27}$N$_5$O$_8$S) |
| 57 | [structure: 2-substituted phenoxy-CH$_2$-pyrrolidine-Nboc with CH$_2$CONHNH$_2$] | [structure: 2-substituted phenoxy-CH$_2$-pyrrolidine-NH] | (DMSO-d6): δ 9.99 (s, 1H), 9.92 (s, 1H), 8.88 (br s, 1H), 8.47 (br s, 1H), 7.22-7.30 (m, 2H), 6.92-7.02 (m, 2H), 4.27-4.31 (m, 1H), 4.07-4.12 (m, 1H), 4.02 (s, 1H), 3.98 (br s, 1H), 3.86 (d, 1H), 3.56 (d, 2H), 3.23-3.30 (m, 2H), 3.21 (d, 1H), 3.01 (d, 1H), 2.09-2.19 (m, 1H), 1.93-1.05 (m, 1H), 1.83-1.92 (m, 2H), 1.65-1.82 (m, 3H), 1.55-1.64 (m, 1H). | 496.3 (M-1) (C$_{20}$H$_{27}$N$_5$O$_8$S) |

TABLE 1-continued

| Example No. | R₁CH₂—CONHNH₂ (Acid hydrazide) | R₁ | ¹H NMR | Mass (Molecular Formula) |
|---|---|---|---|---|
| 58 | [structure: 3-(boc-pyrrolidin-2-ylmethoxy)phenyl-CH₂CONHNH₂] | [structure: 3-(pyrrolidin-2-ylmethoxy)phenyl] | (DMSO-d6): δ 9.99 (s, 1H), 9.90 (s, 1H), 9.10 (br s, 1H), 8.67 (br s, 1H), 7.24 (t, 1H), 6.96 (s, 1H), 6.83-6.92 (m, 2H), 4.08-4.24 (m, 1H), 3.97-4.06 (m, 2H), 3.82-3.89 (m, 1H), 3.80 (d, 1H), 3.44 (s, 2H), 3.12-3.22 (m, 3H), 2.98 (d, 1H), 2.07-2.09 (m, 1H), 1.80-2.05 (m, 4H), 1.53-1.77 (m, 3H). | 496.3 (M-1) (C₂₀H₂₇N₅O₈S) |
| 59 | [structure: 3-(boc-pyrrolidin-2-ylmethoxy)phenyl-CH₂CONHNH₂] | [structure: 3-(pyrrolidin-2-ylmethoxy)phenyl] | (DMSO-d6): δ 10.01 (s, 1H), 9.92 (s, 1H), 9.12 (br s, 1H), 8.69 (br s, 1H), 6.99 (s, 1H), 6.92 (d, 1H), 6.86 (d, 1H), 4.25 (d, 1H), 4.07 (t, 1H), 4.00 (s, 2H), 3.91 (br s, 1H), 3.83 (d, 1H), 3.46 (s, 2H), 3.17 (d, 1H), 3.10-3.16 (m, 2H), 2.99 (d, 1H), 2.13-2.16 (m, 1H), 1.93-2.04 (m, 2H), 1.84-1.92 (m, 2H), 1.69-1.78 (m, 2H), 1.53-1.63 (m, 1H). | 496.3 (M-1) (C₂₀H₂₇N₅O₈S) |
| 60 | [structure: CH₂CONHNH₂ with 3-(boc-pyrrolidin-3-ylmethoxy)phenyl] | [structure: CH₂CONHNH₂ with 3-(pyrrolidin-3-ylmethoxy)phenyl] | (DMSO-d6): δ 10.00 (s, 1H), 9.91 (s, 1H), 8.65 (br s, 2H), 7.23 (t, 1H), 6.94 (s, 1H), 6.88 (d, 1H), 6.77-6.83 (m, 1H), 3.93-4.04 (m, 3H), 2.82 (d, 1H), 3.44 (s, 2H), 3.06-3.24 (m, 3H), 2.96-3.05 (m, 2H), 2.66-2.77 (m, 2H), 2.07-2.13 (m, 2H), 1.98-2.06 (m, 1H), 1.83-1.87 (m, 1H), 1.66-1.81 (m, 2H), 1.53-165 (m, 1H). | 496.3 (M-1) (C₂₀H₂₇N₅O₈S) |
| 61 | [structure: 4-(boc-pyrrolidin-2-ylmethoxy)phenyl-CH₂CONHNH₂] | [structure: 4-(pyrrolidin-2-ylmethoxy)phenyl] | (DMSO-d6): δ 10.20 (br s, 2H), 8.70 (br s, 2H), 7.22 (d, 2H), 6.90 (d, 2H), 4.14-4.18 (m, 1H), 3.97-3.99 (m, 2H), 3.79-3.82 (m, 2H), 3.38 (s, 2H), 3.11-3.21 (m, 3H), 2.97 (d, 1H), 1.63-2.08 (m, 8H). | 496.4 (M-1) (C₂₀H₂₇N₅O₈S) |

TABLE 1-continued

| Example No. | R₁CH₂—CONHNH₂ (Acid hydrazide) | R₁ | ¹H NMR | Mass (Molecular Formula) |
|---|---|---|---|---|
| 62 | CH₂CONHNH₂ attached to 4-(boc-pyrrolidin-2-ylmethoxy)phenyl group | 4-(pyrrolidin-2-ylmethoxy)phenyl group | (DMSO-d6); δ | 496.4 (M-1) ($C_{20}H_{27}N_5O_8S$) |
| 63 | CH₂CONHNH₂ attached to 2-(boc-pyrrolidin-3-yloxy)phenyl group | 2-(pyrrolidin-3-yloxy)phenyl group | (DMSO-d6): δ = 9.97 (s, 1H), 9.90 (s, 1H), 8.91 (br s, 1H), 8.60 (br s, 1H), 7.23-7.28 (m, 2H), 6.92-7.03 (m, 2H), 5.19 (s, 1H), 4.00 (s, 1H), 3.85 (d, 1H), 3.40-3.45 (m, 3H), 3.20-3.39 (m, 3H), 3.19 (d, 1H), 2.99 (d, 1H), 2.13-2.18 (m, 2H), 2.02-2.07 (m, 1H), 1.83-1.86 (m, 1H), 1.69-1.75 (m, 1H), 1.59-1.64 (m, 1H). | 482.3 (M-1) ($C_{19}H_{25}N_5O_8S$) |
| 64 | CH₂CONHNH₂ attached to 4-(boc-pyrrolidin-3-yloxy)phenyl group | 4-(pyrrolidin-3-yloxy)phenyl group | (DMSO-d6): δ = 9.97 (s, 1H), 9.88 (s, 1H), 9.02 (br s, 1H), 8.82 (br s, 1H), 7.25 (d, 2H), 6.91 (d, 2H), 5.11 (s, 1H), 4.00 (s, 1H), 3.82 (d, 1H), 3.41 (s, 2H), 3.28-3.38 (m, 4H), 3.23 (d, 1H), 2.98 (m, 1H), 2.18-2.24 (m, 1H), 2.10-2.13 (m, 1H), 1.99-2.04 (m, 1H), 1.82-1.88 (m, 1H), 1.65-1.76 (m, 1H), 1.53-1.64 (m, 1H). | 482.3 (M-1) ($C_{19}H_{25}N_5O_8S$) |
| 65 | CH₂CONHNH₂ attached to 2-(2-(isobutyryloxy)ethylcarbamate)phenyl group | 2-(2-(isobutyryloxy)ethylcarbamate)phenyl group | (DMSO-d6): δ = 9.86 (br s, 2H), 7.66 (br s, 1H), 7.25 (d, 1H), 7.17-7.22 (m, 1H), 6.86-6.92 (m, 2H), 6.67 (q, 1H), 3.93-3.99 (m, 3H), 3.83 (d, 1H), 3.34-3.45 (m, 4H), 3.25 (d, 1H), 2.98 (d, 1H), 2.47-2.51 (m, 1H), 2.01-2.05 (m, 1H), 1.83-1.87 (m, 1H), 1.60-1.79 (m, 2H), 1.39 (d, 3H), 1.03-1.10 (m, 6H). | 518.5 (M-1); as a free sulfonic acid ($C_{24}H_{32}N_5O_{12}SNa$) |

Biological Activity Data

The biological activity of representative compounds according to the invention against various bacterial strains was investigated. In a typical study, overnight grown bacterial cultures were diluted appropriately and inoculated on the agar media containing doubling dilutions of the test compounds. Observations for growth or no growth was performed after 16-20 hours of incubation at 35±2° C. in the ambient air. The overall procedure was performed as per Clinical and Laboratory Standards Institute (CLSI) recommendations, (Clinical and Laboratory Standards Institute (CLSI), Performance Standards for Antimicrobial Susceptibility Testing, 20$^{th}$ Informational Supplement, M07-A9, Volume 32, No. 2, 2012). Molten Mueller Hinton Agar (BD, USA) containing serial dilutions of each antibacterial agent were poured on to the plates and allowed to solidify. Appropriate suspensions from the freshly grown cultures were prepared in normal saline so that about 10$^4$ CFU/spot of the organism was delivered on to the drug containing agar plates using automated multipoint inoculator (Mast, UK). The plates were incubated in Biochemical oxygen demand (BOD) incubator at 37° C. for 18 hours and then examined for growth.

Table 2 details the antibacterial activity of representative compounds according to invention, against various Multi Drug Resistant (MDR) Gram-negative bacterial strains. The strains selected for study included *E. coli* NCTC 13353 producing CTX-M15 and OXA-1 beta-lactamase enzymes; *K. pneumoniae* H521 producing KPC, SHV, TEM beta-lactamase enzymes; and *K. pneumoniae* S48 producing NDM, SHV, TEM beta-lactamase enzymes. The activities are expressed as Minimum Inhibitory Concentrations (MICs) (mcg/ml). The antibacterial activity profile of representative compounds according to invention were compared against known antibacterial agent such as imipenem and ceftazidime. As can be seen, the MIC values for the representative compounds according to invention were lower in comparison to the standards (imipenem and ceftazidime). Therefore, the results of Table 2 suggests that the compounds of Formula (I) exhibited good antibacterial activity against the multidrug resistant gram negative strains.

TABLE 2

Comparative antibacterial activity of representative compounds according to invention (expressed as MICs (mcg/ml)).

| Compounds | *E. Coli* NCTC 13353 (CTX-M15, OXA-1) | *K. pneumoniae* H521 (KPC, SHV, TEM) | *K. pneomoniae* S48 (NDM, SHV, TEM) |
|---|---|---|---|
| Imipenem | 0.25 | 16 | 16 |
| Ceftazidime | 32 | >32 | >32 |
| Example 1 | 0.5 | 1 | 0.5 |
| Example 2 | 1 | 1 | 1 |
| Example 3 | 1 | 2 | 1 |
| Example 4 | 1 | >32 | 2 |
| Example 5 | 8 | >32 | 8 |
| Example 6 | 16 | >32 | 32 |
| Example 7 | >32 | >32 | >32 |
| Example 8 | 0.5 | 2 | 0.5 |
| Example 9 | 1 | 4 | 1 |
| Example 10 | 1 | 4 | 1 |
| Example 11 | 0.5 | 1 | 1 |
| Example 12 | 0.25 | 0.25 | 0.25 |
| Example 13 | 8 | >32 | 8 |
| Example 14 | 1 | 8 | 1 |
| Example 15 | >32 | >32 | >32 |
| Example 17 | 1 | 4 | 1 |
| Example 18 | 0.5 | 2 | 0.5 |
| Example 19 | 1 | 2 | 2 |
| Example 20 | 0.5 | 1 | 0.5 |
| Example 21 | 16 | 16 | 16 |
| Example 22 | 16 | 32 | 32 |
| Example 23 | 0.5 | 2 | 0.5 |
| Example 24 | 1 | 4 | 0.5 |
| Example 25 | 0.5 | 1 | 1 |
| Example 26 | 2 | 4 | 2 |
| Example 27 | 2 | 16 | 8 |
| Example 28 | 8 | 32 | 16 |
| Example 29 | 4 | 16 | 4 |
| Example 30 | 0.5 | 2 | 0.5 |
| Example 32 | 0.5 | 0.5 | 0.5 |
| Example 34 | 2 | 2 | 2 |
| Example 35 | 0.5 | 1 | 0.5 |
| Example 36 | 1 | 2 | 1 |
| Example 37 | 0.5 | 1 | 0.5 |
| Example 40 | 2 | 2 | 2 |
| Example 41 | 0.5 | 1 | 0.5 |
| Example 42 | 1 | 1 | 0.5 |
| Example 43 | 0.5 | 2 | 0.5 |
| Example 44 | 1 | 2 | 1 |
| Example 46 | 2 | 4 | 4 |
| Example 47 | 1 | 2 | 0.5 |
| Example 49 | 0.5 | 1 | 0.5 |
| Example 50 | 16 | >32 | 16 |
| Example 54 | 1 | 8 | 1 |
| Example 56 | 8 | 16 | 16 |
| Example 57 | 2 | 4 | 2 |
| Example 58 | 1 | 2 | 0.5 |
| Example 60 | 1 | 2 | 1 |
| Example 61 | 1 | 2 | 1 |
| Example 63 | 2 | 8 | 2 |
| Example 64 | 0.5 | 1 | 0.5 |
| Example 65 | >32 | >32 | >32 |

Table 3 details the antibacterial activity of representative compound of Formula (I), Sodium salt of (2S,5R)-Sulfuric acid mono-[2-(N'-(4-hydroxyphenyl-acetyl)-hydrazinocarbonyl)-7-oxo-1,6-diaza-bicyclo[3.2.1]oct-6-yl]ester (Compound of Example 1) and Sodium salt of (2S,5R)-Sulfuric acid mono-[2-(N'-(pyridine-2-yl-acetyl)-hydrazinocarbonyl)-7-oxo-1,6-diaza-bicyclo[3.2.1]oct-6-yl] ester (Compound of Example 8), against various Multi Drug Resistant (MDR) Gram-negative bacterial strains. The activities are expressed as Minimum Inhibitory Concentrations (MICs) (=gimp. As can be seen in Table 3, the MIC values obtained for compounds of Example 1 and Example 8 were found to be lower than those obtained for avibactam. Hence, representative compounds according to invention exhibited good antibacterial activity against various Multi Drug Resistant (MDR) Gram-negative bacterial strains.

Determination of enzyme inhibition activity: Concentration of the inhibitor required to inhibit 50% of enzymatic activity was measured by adding a chromogenic substrate, Nitrocefin (100 uM, 5 min) to the preincubated mixture of crude enzyme and the agents (37° C., 10 min). Absorbance was measured at 485 nm by UV-spectrophotometer. The IC$_{50}$ was calculated by plotting absorbance against concentration through Sigmoidal dose response curve using Graph Pad software.

The Table 4 provides the beta-lactamase enzyme inhibition activity of representative compounds of Formula (I), against Multi Drug Resistant Gram-negative bacterial strains expressing various ESBLs. The enzyme inhibition was expressed as $IC_{50}$. As can be seen from the data of Table 4, the beta-lactamase enzyme inhibition values for the compounds according to invention were found to be lower than avibactam and clavulanic acid. The compounds according to invention exhibited potent antibacterial activity against wide variety of bacteria producing Class A, Class C and Class D types of beta-lactamase enzymes. In general, representative compound according to invention exhibited better activity against Class C and Class D beta-lactamase producing bacterial strains than the other currently employed antibacterial agents (for example avibactam and clavulanic acid).

TABLE 3

Antibacterial activity Sodium salt of (2S,5R)-Sulfuric acid mono-[2-(N'-(4-hydroxyphenyl-acetyl)-hydrazinocarbonyl)-7-oxo-1,6-diaza-bicyclo[3.2.1] oct-6-yl] ester (Compound of Example 1) and Sodium salt of (2S,5R)-Sulfuric acid mono-[2-(N'-(pyridine-2-yl-acetyl)-hydrazinocarbonyl)-7-oxo-1,6-diaza-bicyclo[3.2.1]oct-6-yl] ester (Compound of Example 8) against various Gram negative bacterial strains.

| Organism | MIC (mcg/ml) | | |
|---|---|---|---|
| | Compound of Example 1 | Compound of Example 2 | Avibactam |
| E. coli NCTC 13351 | 0.25 | 1 | >64 |
| E. coli NCTC 13352 | 0.25 | 1 | >64 |
| E. coli NCTC 13353 | 0.5 | 0.5 | 16 |
| E. coli M 49 | 2 | 2 | 16 |
| E. coli M 50 | 0.5 | 1 | >64 |
| E. coli 7 MP | 1 | 2 | >64 |
| C. frundaii 58 MP | 32 | 16 | >64 |
| E. cloacae M 20 | 1 | 2 | >64 |
| K. pneumoniae H 521 | 1 | 2 | 16 |
| K. pneumoniae H 525 | 0.5 | 1 | 8 |
| K. pneumoniae B 88 | 0.5 | >32 | 32 |
| K. pneumoniae S 21 | 2 | 2 | 16 |
| P. aeruginosa PAO1 | >32 | >32 | >64 |
| P. aeruginosa ATCC 27853 | >32 | >32 | >64 |
| P. aeruginosa R 20 | >32 | >32 | >64 |
| P. aeruginosa 2779 | >32 | >32 | >64 |

Determination of antibacterial activity of combinations according to invention: In a typical experiment, two sets of plates containing growth media (Molten Mueller Hilton Agar) and bacterial strains were prepared. One set of plates was taken as control (without ceftazidime) and other set contained ceftazidime. The media was allowed to solidify and wells were punched later. A two-fold serial dilution range of each of the compounds according to invention was prepared and 50 µl of each of the dilution was added into the punched well. The plates were then incubated at 37° C. for 18 hours in BOD incubator and diameters of zone of inhibition were measured after the completion of the incubation.

The Table 5 provides the antibacterial activity of the combination comprising compounds according to invention and ceftazidime. The compounds according to invention were tested at 0.12, 0.25, 0.5 and 1 µg/well. As can be seen from the results of the Table 5 the diameter to zone of inhibition significantly increased in presence of ceftazidime. The compounds according to invention exhibited synergistic antibacterial activity in presence of ceftazidime.

The results of Tables 1 to 5 clearly demonstrate potent antibacterial activity of compounds of according to the invention against highly resistant gram negative bacteria producing ESBLs. Thus, the compounds of Formula (I) has tremendous beneficial effect in inhibiting highly resistant bacterial strains demonstrating the noteworthy therapeutic advance in the treatment of infections caused by such pathogens.

TABLE 4

Beta-lactamase enzyme inhibition activity of representative compounds of Formula (I) against bacterial strains producing ESBLs (expressed as $IC_{50}$ (µM))

| Compound | Class A K. pneumoniae ATCC 700603 (SHV 18) | Class C E. coli M50 (CMY/DHA) | Class D A. baumannii NCTC 13301 (OXA 23) |
|---|---|---|---|
| Avibactam | 0.098 | 0.146 | 9.735 |
| Clavulanic acid | 0.021 | >10 | >10 |
| Example 1 | 0.103 | 0.005 | 0.315 |
| Example 2 | 0.119 | 0.122 | 3.766 |
| Example 3 | 0.080 | 0.073 | 2.015 |
| Example 4 | 0.019 | 0.009 | 0.416 |
| Example 5 | 0.009 | 0.030 | 0.60 |
| Example 6 | — | 0.009 | 0.207 |
| Example 7 | 0.07 | 0.014 | 0.089 |
| Example 8 | 0.025 | 0.012 | 0.466 |
| Example 9 | — | 0.011 | 0.173 |
| Example 10 | 0.162 | 0.028 | 0.805 |
| Example 11 | 0.032 | 0.010 | 0.408 |
| Example 12 | 0.144 | 0.013 | 0.539 |
| Example 13 | 0.062 | 0.017 | 0.629 |
| Example 14 | — | 0.013 | 0.105 |
| Example 15 | 0.049 | 0.007 | 0.210 |
| Example 17 | 0.018 | 0.014 | 0.194 |
| Example 18 | 0.154 | 0.012 | 0.146 |
| Example 19 | 0.013 | 0.013 | 0.677 |
| Example 20 | 0.012 | 0.011 | 0.249 |
| Example 21 | 0.035 | 0.034 | 4.51 |
| Example 22 | 0.025 | 0.021 | 0.973 |
| Example 23 | 0.003 | 0.023 | 0.24 |
| Example 24 | 0.002 | 0.005 | 0.151 |
| Example 25 | 0.016 | 0.011 | 0.329 |
| Example 26 | 0.025 | 0.010 | 0.370 |
| Example 27 | 0.018 | 0.014 | 0.498 |
| Example 28 | 0.008 | 0.014 | 0.243 |
| Example 29 | 0.327 | 0.085 | 2.85 |
| Example 30 | 0.007 | 0.036 | 0.451 |
| Example 32 | 0.076 | 0.033 | 1.77 |
| Example 34 | 0.079 | 0.06 | 3.81 |
| Example 35 | 0.712 | 0.038 | 1.907 |
| Example 36 | 0.071 | 0.070 | 2.170 |
| Example 37 | 0.036 | 0.017 | 0.938 |
| Example 40 | 0.11 | 0.099 | 1.57 |
| Example 41 | 0.038 | 0.053 | 0.990 |
| Example 42 | 0.036 | 0.032 | 1.225 |
| Example 43 | 0.386 | 0.037 | 0.522 |
| Example 44 | 0.058 | 0.031 | 0.561 |
| Example 46 | 0.079 | 0.266 | 4.098 |
| Example 47 | 0.0151 | 0.077 | 0.842 |
| Example 49 | 0.112 | 0.047 | 0.542 |
| Example 50 | 0.079 | 0.077 | 1.166 |
| Example 54 | 0.037 | 0.040 | 0.625 |
| Example 56 | 0.142 | 0.05 | 1.76 |
| Example 57 | 0.125 | 0.105 | 3.293 |
| Example 58 | 0.053 | 0.037 | 1.469 |
| Example 60 | 0.045 | 0.041 | 1.280 |
| Example 61 | 0.071 | 0.029 | 0.690 |
| Example 63 | 0.079 | 0.102 | 4.12 |
| Example 64 | 0.047 | 0.028 | 0.432 |
| Example 65 | 0.008 | 0.005 | 0.537 |

TABLE 5

Antibacterial activity of combination comprising compounds according to invention and Ceftazidime.

| | | Diameter of Zone of Inhibition (mm) | | | |
|---|---|---|---|---|---|
| | | E. coli NCTC 13353 | | E. coli M50 | |
| Compounds of Formula (I) | Concentrations (μg/well) | Compound | Compound + Ceftazidime (10 μg/ml) | Compound | Compound + Ceftazidime (10 μg/ml) |
| Example 1 | 0.12 | 12.5 | 16 | 9 | 13 |
| | 0.25 | 14.5 | 18 | 12 | 16 |
| | 0.5 | 15.5 | 21 | 13.5 | 19 |
| | 1 | 17 | 25 | 16 | 22 |
| Example 2 | 0.12 | No growth | 17 | No growth | 10 |
| | 0.25 | 11 | 21 | 10 | 13 |
| | 0.5 | 14 | 24 | 14 | 16.5 |
| | 1 | 16 | 28 | 16 | 18.5 |
| Example 3 | 0.12 | No growth | 11 | No growth | No growth |
| | 0.25 | No growth | 14.5 | No growth | 10.5 |
| | 0.5 | 10 | 17.5 | 11.5 | 14 |
| | 1 | 13 | 21.5 | 14 | 17 |
| Example 12 | 0.12 | 14.5 | 19 | 13 | 16 |
| | 0.25 | 15.5 | 22 | 15 | 19 |
| | 0.5 | 17 | 26 | 18 | 21 |
| | 1 | 19 | 29 | 19.5 | 23 |

The invention claimed is:

1. A compound of Formula (I):

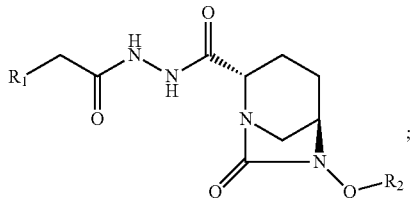

Formula (I)

a stereoisomer thereof or a pharmaceutically acceptable salt thereof;
wherein:
$R_1$ is aryl substituted with one or more substituents independently selected from $C_1$-$C_6$ alkyl, halogen, CN, $OR_3$, $N(C_1$-$C_6$ alkyl)$R_3$, $CH_2NH_2$ or $CONR_3R_4$;
$R_2$ is $SO_3M$;
$R_3$ and $R_4$ are each independently:
  (a) hydrogen, or
  (b) $C_1$-$C_6$ alkyl, optionally substituted with one or more substituents independently selected from:
    (i) halogen,
    (ii) CN,
    (iii) OH,
    (iv) O($C_1$-$C_6$ alkyl),
    (v) NH($C_1$-$C_6$ alkyl),
    (vi) N($C_1$-$C_6$ alkyl)$_2$,
    (viii) CO—N($C_1$-$C_6$ alkyl)$_2$,
    (ix) cycloalkyl,
    (x) heterocycloalkyl,
    (xi) aryl,
    (xii) heteroaryl,
    (xiii) $NH_2$, or
    (xiv) NH—CO—O—($C_1$-$C_6$ alkyl, optionally substituted with —CO—O—C(CH$_3$)$_3$);
  (c) heterocycloalkyl;
  (d) CO—($C_1$-$C_6$ alkyl, optionally substituted with $NH_2$ or —CO—O—C(CH$_3$)$_3$);
  (e) CO-(heterocycloalkyl);
  (f) CO—NH—($C_1$-$C_6$ alkyl, optionally substituted with —CO—O—CH(CH$_3$)$_2$); or
  (g) CO—NH-(cycloalkyl);
wherein M is hydrogen or a cation.

2. The compound according to claim 1, wherein said compound is selected from:
(2S,5R)-sulfuric acid mono-[2-(N'-(4-hydroxyphenyl-acetyl)-hydrazinocarbonyl)-7-oxo-1,6-diaza-bicyclo[3.2.1]oct-6-yl]ester;
(2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-(4-chlorophenyl-acetyl)-hydrazinocarbonyl)-7-oxo-1,6-diaza-bicyclo[3.2.1]oct-6-yl]ester;
(2S,5R)-sulfuric acid mono-[2-(N'-(4-cyanophenyl-acetyl)-hydrazinocarbonyl)-7-oxo-1,6-diaza-bicyclo[3.2.1]oct-6-yl]ester;
(2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester;
(2S,5R)-sulfuric acid mono-[2-(N'-(4-N,N-dimethylaminophenyl-acetyl)-hydrazinocarbonyl)-7-oxo-1,6-diaza-bicyclo[3.2.1]oct-6-yl]ester;
(2S,5R)-sulfuric acid mono-[2-(N'-(4-methoxyphenyl-acetyl)-hydrazinocarbonyl)-7-oxo-1,6-diaza-bicyclo[3.2.1]oct-6-yl]ester;
(2S,5R)-sulfuric acid mono-[2-(N'-(2-ethoxyphenyl-acetyl)-hydrazinocarbonyl)-7-oxo-1,6-diaza-bicyclo[3.2.1]oct-6-yl]ester;
(2S,5R)-sulfuric acid mono-[2-(N'-(2-fluoro-4-ethoxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(4-amino-2-fluorophenyl-acetyl)-hydrazinocarbonyl)-7-oxo-1,6-diaza-bicyclo[3.2.1]oct-6-yl]ester;

(2S,5R)-sulfuric acid mono-[2-(N'-(2-fluoro-4-hydroxyphenyl-acetyl)-hydrazinocarbonyl)-7-oxo-1,6-diazabicyclo[3.2.1]oct-6-yl]ester;

(2S,5R)-sulfuric acid mono-[2-(N'-(2-hydroxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(3-hydroxyphenyl-acetyl)-hydrazinocarbonyl)-7-oxo-1,6-diaza-bicyclo[3.2.1]oct-6-yl]ester;

(2S,5R)-sulfuric acid mono-[2-(N'-(2-aminophenyl-acetyl)-hydrazinocarbonyl)-7-oxo-1,6-diaza-bicyclo[3.2.1]oct-6-yl]ester;

2,2-dimethyl-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(S)-2-amino-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(S)-2-amino-3-methyl-butyric acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(S)-pyrrolidine-2-carboxylic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;

(2S,5R)-malonic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;

(2S,5R)-succinic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;

(2S,5R)-cyclohexyl-carbamic acid 4-{2-oxo-2-[N'-(7-oxo-6-sulphooxy-1,6-diaza-bicyclo[3.2.1]octane-2-carbonyl)-hydrazino]ethyl}-phenyl ester;

3-methyl-2-(4-{2-oxo-2-[N'-(7-oxo-6-sulphooxy-1,6-diaza-bicyclo[3.2.1]octane-2-carbonyl)-hydrazino]-ethyl}-phenoxycarbonylamino)-butyric acid tert-butyl ester;

(S)-3-methyl-2-(4-{2-oxo-2-[N'-((2S,5R)-7-oxo-6-sulphooxy-1,6-diaza-bicyclo[3.2.1]-ocatne-2-carbonyl)-hydrazino]-ethyl}-phenoxycarbonylamino)-butyric acid tert-butyl ester;

(2S,5R)-sulfuric acid mono-[2-(N'-(2-fluoro-4-(2-amino-ethoxy)-phenyl-acetyl)-hydrazinocarbonyl)-7-oxo-1,6-diaza-bicyclo[3.2.1]oct-6-yl]ester;

(2S,5R)-sulfuric acid mono-[2-(N'-{2-[3-(2-amino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-(2-hydroxy-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-(3-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-(3-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-(2-N-methyl-amino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-(2-N-methyl-amino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-(2-N-methyl-amino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-(2-N-methylamino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((R)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((S)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((R)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((R)-2-amino-3-methyl-butoxy)-phenyl[-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((S)-pyrrolidin-3-oxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-((R)-pyrrolidin-2-ylmethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((R)-2-amino-propoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((S)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-((R)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((S)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[3-((R)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((S)-2-amino-3-methyl-butoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[4-((R)-2-amino-3-methyl-butoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[2-((S)-pyrrolidin-2-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[2-((R)-pyrrolidin-2-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[3-((S)-pyrrolidin-2-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[3-((R)-pyrrolidin-2-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[3-((R)-pyrrolidin-3-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[4-((S)-pyrrolidin-2-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[4-((R)-pyrrolidin-2-ylmethoxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[2-((S)-pyrrolidin-3-oxy)-phenyl]-acetyl}-hydrazinocarbonyl)-7-oxo-1,6-diaza-bicyclo[3.2.1]oct-6-yl]ester;
(2S,5R)-sulfuric acid mono-[2-(N'-{2-[4-((S)-pyrrolidin-3-oxy)-phenyl]-acetyl}-hydrazinocarbonyl)-7-oxo-1,6-diaza-bicyclo[3.2.1]oct-6-yl]ester;
isobutyric acid 1-[2-(2-{2-oxo-2-[N'-((2S,5R)-6-sulphooxy-7-oxo-1,6-diaza-bicyclo[3.2.1]octane-2-carbonyl)-hydrazino]-ethyl}-phenoxy)-ethylcarbamoyloxy]-ethyl ester;
a stereoisomer thereof or a pharmaceutically acceptable salt thereof.

3. The compound according to claim 1, wherein said compound is selected from:
sodium salt of (2S,5R)-sulfuric acid mono-[2-(N'-(4-hydroxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester;
sodium salt of (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester;
sodium salt of (2S,5R)-sulfuric acid mono-[2-(N'-(4-chlorophenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(4-cyanophenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(4-N,N-dimethylaminophenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(4-methoxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(2-ethoxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(2-fluoro-4-ethoxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(4-amino-2-fluorophenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N-(2-fluoro-4-hydroxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(2-hydroxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(3-hydroxyphenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-(2-aminophenyl-acetyl)-hydrazinocarbonyl)-7-oxo-1,6-diaza-bicyclo[3.2.1]oct-6-yl]ester;
sodium salt of 2,2-dimethyl-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;
sodium salt of (S)-2-amino-propionic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;
sodium salt of (S)-2-amino-3-methyl-butyric acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;
sodium salt of (S)-pyrrolidine-2-carboxylic acid 4-{2-oxo-2-[N'-((2S,5R)-7-oxo-6-sulphooxy-1,6-diaza-bicyclo[3.2.1]octane-2-carbonyl)-hydrazino]ethyl}-phenyl ester;
sodium salt of (2S,5R)-malonic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;
sodium salt of (2S,5R)-succinic acid tert-butyl ester 4-{2-oxo-2-[N'-(7-oxo-6-sulphooxy-1,6-diaza-bicyclo[3.2.1]octane-2-carbonyl)-hydrazino]ethyl}-phenyl ester;
sodium salt of (2S,5R)-cyclohexyl-carbamic acid 4-{2-oxo-2-[N'-(7-oxo-6-sulphooxy-1,6-diaza-bicyclo[3.2.1]octane-2-carbonyl)-hydrazino]ethyl}-phenyl ester;
sodium salt of 3-methyl-2-(4-{2-oxo-2-[N'-(7-oxo-6-sulphooxy-1,6-diaza-bicyclo[3.2.1]octane-2-carbonyl)-hydrazino]-ethyl}-phenoxycarbonylamino)-butyric acid tert-butyl ester;
sodium salt of (S)-3-methyl-2-(4-{2-oxo-2-[N'-((2S,5R)-7-oxo-6-sulphooxy-1,6-diaza-bicyclo[3.2.1]-ocatne-2-carbonyl)-hydrazino]-ethyl}-phenoxycarbonylamino)-butyric acid tert-butyl ester;
sodium salt of (2S,5R)-sulfuric acid mono-[2-(N'-(2-fluoro-4-(2-amino-ethoxy)-phenyl-acetyl)-hydrazinocarbonyl)-7-oxo-1,6-diaza-bicyclo[3.2.1]oct-6-yl]ester;
sodium salt of (2S,5R)-sulfuric acid mono-[2-(N'-{2-[3-(2-amino-ethoxy)-phenyl]-acetyl}-hydrazinocarbonyl)-7-oxo-1,6-diaza-bicyclo[3.2.1]oct-6-yl]ester;
sodium salt of (2S,5R)-sulfuric acid mono-[2-(N'-{2-[2-(2-hydroxy-ethoxy)-phenyl]-acetyl}-hydrazinocarbonyl)-7-oxo-1,6-diaza-bicyclo[3.2.1]oct-6-yl]ester;
sodium salt of (2S,5R)-sulfuric acid mono-[2-(N'-{2-[2-(3-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-(3-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-(2-N-methylamino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-(2-N-methylamino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-(2-N-methylamino-ethoxy)-phenyl]-acetyl}-hydrazinocarbonyl)-7-oxo-1,6-diaza-bicyclo[3.2.1]oct-6-yl]ester;

(2S,5R)-sulfuric acid mono-[2-(N'-{2-[2-fluoro-4-(2-N-methylamino-ethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((S)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-fluoro-4-((R)-2-amino-3-methyl-butoxy)-phenyl]-acetyl}-hydrazinocarbonyl)-7-oxo-1,6-diaza-bicyclo[3.2.1]oct-6-yl] ester;

sodium salt of (2S,5R)-sulfuric acid mono-[2-(N-{2-[2-fluoro-4-((S)-pyrrolidin-3-oxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N-{2-[2-fluoro-4-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N-{2-[4-((R)-2-amino-propoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((S)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((R)-2-amino-3-methyl-butoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((S)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[3-((R)-pyrrolidin-3-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((S)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[4-((R)-pyrrolidin-2-ylmethoxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N'-{2-[2-((S)-pyrrolidin-3-oxy)-phenyl]-acetyl}-hydrazinocarbonyl)-7-oxo-1,6-diaza-bicyclo[3.2.1]oct-6-yl]ester;

sodium salt of (2S,5R)-sulfuric acid mono-[2-(N-{2-[4-((S)-pyrrolidin-3-oxy)-phenyl]-acetyl}-hydrazinocarbonyl)-7-oxo-1,6-diaza-bicyclo[3.2.1]oct-6-yl]ester;

sodium salt of isobutyric acid 1-[2-(2-{2-oxo-2-[N'-((2S,5R)-6-sulphooxy-7-oxo-1,6-diaza-bicyclo[3.2.1]octane-2-carbonyl)-hydrazino]-ethyl}-phenoxy)-ethyl-carbamoyloxy]-ethyl ester;

a stereoisomer thereof or a pharmaceutically acceptable salt thereof.

4. A pharmaceutical composition comprising a compound of Formula (I) according to claim 1.

5. The pharmaceutical composition according to claim 4, wherein a compound of Formula (I) is:

(2S,5R)-sulfuric acid mono-[2-(N'-{2-[4-(2-amino-ethoxy)-phenyl]-acetyl}-hydrazinocarbonyl)-7-oxo-1,6-diaza-bicyclo[3.2.1]oct-6-yl]ester, (2S,5R)-sulfuric acid mono-[2-(N'-{2-[2-((R)-2-amino-propoxy)-phenyl]-acetyl}-hydrazinocarbonyl)-7-oxo-1,6-diaza-bicyclo[3.2.1]oct-6-yl]ester, (2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester, a stereoisomer thereof or a pharmaceutically acceptable salt thereof.

6. The pharmaceutical composition according to claim 4, further comprising at least one beta-lactamase inhibitor, or a pharmaceutically acceptable salt thereof.

7. The pharmaceutical composition according to claim 4, further comprising at least one antibacterial agent, or a pharmaceutically acceptable salt thereof.

8. The pharmaceutical composition according to claim 7, wherein the antibacterial agent is selected from the group consisting of aminoglycosides, ansamycins, carbacephems, cephalosporins, cephamycins, lincosamides, lipopeptides, macrolides, monobactams, nitrofurans, penicillins, penems, carbapenems, polypeptides, quinolones, sulfonamides, tetracyclines, oxazolidinones, and beta-lactam antibacterial agents.

9. The pharmaceutical composition according to claim 7, wherein the antibacterial agent is a cephalosporin antibiotic; wherein said cephalosporin antibiotic is selected from the group consisting of cephalotin, cephaloridine, cefaclor, cefadroxil, cefamandole, cefazolin, cefalexin, cefradine, ceftizoxime, cefoxitin, cephacetrile, cefotiam, cefotaxime, cefsulodin, cefoperazone, cefmenoxime, cefmetazole, cepfaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime auxetil, cefpodoxime proxetil, cefteram pivoxil, cefetamet pivoxil, cefcapene pivoxil, cefditoren pivoxel, cefuroxime, cefuroxime auxetil, loracarbacef, ceftaroline, ceftolozane and latamoxef.

10. A method for treating a bacterial infection in a subject, wherein said method comprises administering to the subject the pharmaceutical composition according to claim 4.

11. A method for treating a bacterial infection in a subject, wherein said method comprises administering to the subject a compound of Formula (I) according to the claim 1.

12. A method according to claim 11, wherein compound of Formula (I) is selected from:
(2S,5R)-sulfuric acid mono-[2-(N'-{2-[4-(2-aminoethoxy)-phenyl]-acetyl}-hydrazinocarbonyl)-7-oxo-1,6-diaza-bicyclo[3.2.1]oct-6-yl]ester,
(2S,5R)-sulfuric acid mono-[2-(N'-{2-[2-((R)-2-aminopropoxy)-phenyl]-acetyl}-hydrazinocarbonyl)-7-oxo-1,6-diaza-bicyclo[3.2.1]oct-6-yl]ester,
(2S,5R)-sulfuric acid mono-[2-(N'-(4-aminomethyl-phenyl-acetyl)-hydrazinocarbonyl)-7-oxo-1,6-diaza-bicyclo[3.2.1]oct-6-yl]ester,
a stereoisomer or a pharmaceutically acceptable salt thereof.

13. A method for treating a bacterial infection in a subject, wherein said method comprises administering to said subject a pharmaceutical composition comprising: (a) compounds according to claim 1; and (b) at least one beta-lactamase inhibitor or a pharmaceutically acceptable salt thereof.

14. A method for treating a bacterial infection in a subject, wherein said method comprises administering to the subject a pharmaceutical composition comprising: (a) compounds according to claim 1; and (b) at least one antibacterial agent or a pharmaceutically acceptable salt thereof.

15. A method for treating a bacterial infection in a subject, wherein said method comprising administering to the subject a pharmaceutical composition comprising: (a) compounds according to claim 1; and (b) at least one antibacterial agent selected from cefepime, cefpirome, ceftaroline, ceftazidime, ceftalozane or a pharmaceutically acceptable salt thereof.

16. A method for treating a bacterial infection in a subject, wherein said method comprises administering to the subject: (a) a compound according to claim 1, and (b) at least one beta-lactamase inhibitor, or a pharmaceutically acceptable salt thereof.

17. A method for treating a bacterial infection in a subject, wherein said method comprises administering to the subject: (a) a compound according to claim 1, and (b) at least one antibacterial agent, or a pharmaceutically acceptable salt thereof.

18. A process for the preparation of a compound of Formula (I):

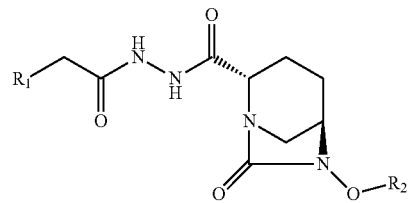

Formula (I)

wherein $R_1$ is aryl optionally substituted with one or more substituents independently selected from $C_1$-$C_6$ alkyl, halogen, CN, $OR_3$, $N(C_1$-$C_6$ alkyl)$R_3$, $CH_2NH_2$ or $CONR_3R_4$;

wherein $R_2$ is $SO_3M$;

wherein $R_3$ and $R_4$ are each independently:
(a) hydrogen, or
(b) $C_1$-$C_6$ alkyl, optionally substituted with one or more substituents independently selected from:
(i) halogen,
(ii) CN,
(iii) OH,
(iv) O($C_1$-$C_6$ alkyl),
(v) NH($C_1$-$C_6$ alkyl),
(vi) N($C_1$-$C_6$ alkyl)$_2$,
(viii) CO—N($C_1$-$C_6$ alkyl)$_2$,
(ix) cycloalkyl,
(x) heterocycloalkyl,
(xi) aryl,
(xii) heteroaryl,
(xiii) $NH_2$, or
(xiv) NH—CO—O—($C_1$-$C_6$ alkyl, optionally substituted with —CO—O—$C(CH_3)_3$);
(c) heterocycloalkyl;
(d) CO—($C_1$-$C_6$ alkyl, optionally substituted with $NH_2$ or —CO—O—$C(CH_3)_3$);
(e) CO-(heterocycloalkyl);
(f) CO—NH—($C_1$-$C_6$ alkyl, optionally substituted with —CO—O—$CH(CH_3)_2$); or
(g) CO—NH-(cycloalkyl);

wherein M is hydrogen or a cation;

wherein said process comprising:
(a) reacting a compound of Formula (Ia) with $R_1CONHNH_2$ (Ib), in presence of a coupling agent, to obtain a compound of Formula (Ic):

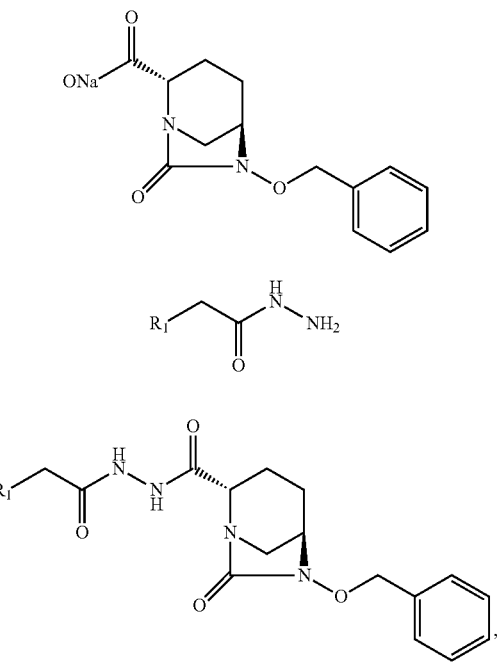

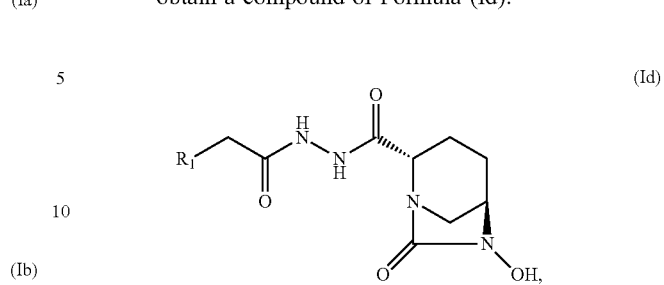

(b) hydrogenolysis of a compound of Formula (Ic) to obtain a compound of Formula (Id):

and (c) sulfonating a compound of Formula (Id), and obtaining the compound of Formula (I).

19. The process according to claim 18; wherein the coupling agent in step (a) is selected from 1-ethyl-3-(3-dimethylaminopropyl)carbodiimide hydrochloride, 1-hydroxybenzotriazole, dicyclohexyl carbodiimde or pivalyl chloride.

20. The process according to claim 18; wherein the sulfonation in step (c) is carried in presence of sulfur trioxide-pyridine complex or sulfur trioxide-N, N-dimethylformamide complex.

* * * * *